US012723229B2

(12) United States Patent
Higuchi

(10) Patent No.: US 12,723,229 B2
(45) Date of Patent: Sep. 1, 2026

(54) CULTURE DEVICE

(71) Applicant: CANON KABUSHIKI KAISHA, Tokyo (JP)

(72) Inventor: Akira Higuchi, Toyonaka (JP)

(73) Assignee: Canon Kabushiki Kaisha, Tokyo (JP)

( * ) Notice: Subject to any disclaimer, the term of this patent is extended or adjusted under 35 U.S.C. 154(b) by 670 days.

(21) Appl. No.: 18/005,777

(22) PCT Filed: Jul. 29, 2021

(86) PCT No.: PCT/JP2021/028181

§ 371 (c)(1),
(2) Date: Jan. 17, 2023

(87) PCT Pub. No.: WO2022/030365

PCT Pub. Date: Feb. 10, 2022

(65) Prior Publication Data

US 2023/0279331 A1 Sep. 7, 2023

(30) Foreign Application Priority Data

Aug. 4, 2020 (JP) ................................ 2020-132656

(51) Int. Cl.
*C12M 1/34* (2006.01)
*C12M 1/00* (2006.01)

(52) U.S. Cl.
CPC ............ *C12M 41/34* (2013.01); *C12M 29/04* (2013.01); *C12M 29/16* (2013.01); *C12M 29/20* (2013.01);
(Continued)

(58) Field of Classification Search
None
See application file for complete search history.

(56) References Cited

U.S. PATENT DOCUMENTS 4,301,252 A * 11/1981 Baker .................... C12M 23/54 435/303.1
5,627,070 A * 5/1997 Gruenberg ............. C12M 41/26 435/286.5
(Continued)

FOREIGN PATENT DOCUMENTS

EP 3252137 12/2017
JP H2-207782 8/1990
(Continued)

OTHER PUBLICATIONS

Cui et al., High-density culture of Lactobacillus plantarum coupled with a lactic acid removal system with anion-exchange resins, Biochemical Engineering Journal, 115 (2016) 80-84 (Year: 2016).*
(Continued)

*Primary Examiner* — Holly Kipouros
(74) *Attorney, Agent, or Firm* — Venable LLP

(57) ABSTRACT

A culture device includes a culture vessel that contains a culture solution for culturing cells, a gas supply device that supplies a gas to the culture vessel, and a humidification device that humidifies the gas flowing from the gas supply device to the culture vessel. The humidification device includes a hollow fiber membrane filter that includes a hollow fiber membrane through which the gas from the gas supply device passes and a casing that accommodates the hollow fiber membrane, a water supply device that fills the casing of the hollow fiber membrane filter with water, and a first heater that heats the hollow fiber membrane filter.

19 Claims, 13 Drawing Sheets

(52) U.S. Cl.
CPC ............ *C12M 29/26* (2013.01); *C12M 41/12* (2013.01); *C12M 41/44* (2013.01)

(56) References Cited

U.S. PATENT DOCUMENTS

| | | | | |
|---|---|---|---|---|
| 2016/0090568 | A1 | 3/2016 | Jeong et al. | |
| 2018/0016534 | A1 | 1/2018 | Matsuda | |
| 2020/0009348 | A1 | 1/2020 | Sunada et al. | |
| 2020/0131460 | A1 | 4/2020 | Higuchi et al. | |
| 2020/0181551 | A1* | 6/2020 | Lee .................... | G01N 33/5088 |

FOREIGN PATENT DOCUMENTS

| | | |
|---|---|---|
| JP | 2005-331862 | 12/2005 |
| JP | 2014-001898 | 1/2014 |
| JP | 2017-529106 | 10/2017 |
| JP | 2019-000043 | 1/2019 |
| WO | 2016/050544 | 4/2016 |
| WO | 2016/120708 | 8/2016 |
| WO | 2021/002358 | 1/2021 |

OTHER PUBLICATIONS

Notice of Reasons for Refusal in Japanese Application No. 2022-541495 (Jul. 2025).
International Preliminary Report on Patentability of PCT/JP2021/028181, Feb. 16, 2023, 14 pages including English translation.
International Search Report of PCT/JP2021/028181, Oct. 19, 2021, 7 pages including English translation.

* cited by examiner

Ge
90
100
98
94
Pout
292
212a
CS
212
212c
224
Pin
278
212b
80
88
Gw
76
86
78
62
66
66
64
68
60
Gd
X
Z
Y

CULTURE DEVICE

TECHNICAL FIELD

The present invention relates to a culture device that cultures cells using a culture solution in a culture vessel.

BACKGROUND ART

For example, Patent Document 1 discloses a shaking-type culture device that cultures cells using a culture solution in a culture bag (culture vessel). This culture device cultures the cells in the culture vessel by shaking this culture vessel while heating the culture vessel with a rubber heater or the like. Furthermore, this culture device cultures the cells while supplying a mixed gas into the culture vessel.

PRIOR ART DOCUMENTS

Patent Documents

Patent Document 1: WO 2016/120708 A1

SUMMARY OF THE INVENTION

Problems to be Solved by the Invention

When the cells are cultured using a culture solution in the culture vessel as in the culture device described in Patent Document 1, evaporation of the culture solution is a problem in some cases. When the culture solution evaporates, an osmotic pressure of the culture solution increases, water flows out of the cells, and thereby the cells are damaged. In particular, when cells are cultured by using a small amount of culture solution, an evaporation percentage of the culture solution increases, therefore the osmotic pressure also increases, and thereby the cells are greatly damaged.

It is therefore an object of the present invention to suppress evaporation of a culture solution when cells are cultured using the culture solution in a culture vessel.

Means for Solving the Problems

In order to solve the above technical problem, according to one aspect of the present invention, there is provided culture device that includes:

- a culture vessel that contains a culture solution for culturing cells;
- a gas supply device that supplies a gas to the culture vessel; and
- a humidification device that humidifies the gas flowing from the gas supply device to the culture vessel, and in which the humidification device includes

- a hollow fiber membrane filter that includes a hollow fiber membrane through which the gas from the gas supply device passes, and a casing that accommodates the hollow fiber membrane,
- a water supply device that fills the casing of the hollow fiber membrane filter with water, and
- a first heater that heats the hollow fiber membrane filter.

Effects of the Invention

According to the present invention, it is possible to suppress evaporation of a culture solution when cells are cultured using the culture solution in a culture vessel.

MODE(S) FOR CARRYING OUT THE INVENTION

Figure 1:
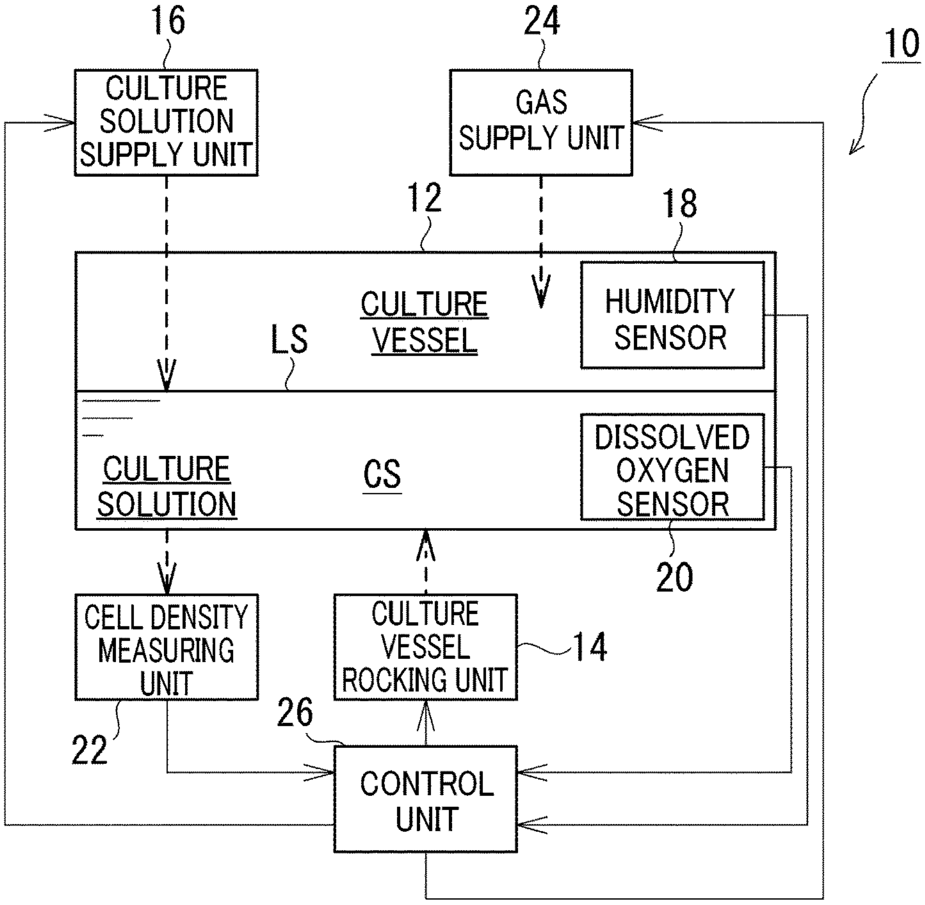
FIG. 1 is a schematic configuration diagram illustrating a configuration of a culture device according to an embodiment of the present invention.

A culture device according to one aspect of the present invention includes a culture vessel that contains a culture solution for culturing cells, a gas supply device that supplies a gas to the culture vessel, and a humidification device that humidifies the gas flowing from the gas supply device to the culture vessel, and the humidification device includes a hollow fiber membrane filter that includes a hollow fiber membrane through which the gas from the gas supply device passes, and a casing that accommodates the hollow fiber membrane, a water supply device that fills the casing of the hollow fiber membrane filter with water, and a first heater that heats the hollow fiber membrane filter.

According to this aspect, it is possible to suppress evaporation of this culture solution when the cells are cultured using the culture solution in the culture vessel.

For example, the culture device includes a second heater that is disposed below the culture vessel and heats the culture solution in the culture solution. In this case, a heating temperature of the first heater is higher than a heating temperature of the second heater. Consequently, water vapor in the gas having flown out of the humidification device is suppressed from condensing and decreasing before reaching the culture vessel.

For example, the culture device includes a first membrane filter that is provided in a gas supply channel between the humidification device and the culture vessel and disposed in a state where a normal line of a filter surface is tilted with respect to a vertical direction. This first membrane filter suppresses contamination of the culture solution in the culture vessel. Furthermore, the tilt suppresses condensed water from uniformly spreading over the entire filter surface of the first membrane filter, and a flow resistance from increasing.

For example, the culture device includes a third heater that heats the first membrane filter. In this case, a heating temperature of the third heater is higher than a heating temperature of the first heater. Consequently, the water vapor in the gas can pass through the first membrane filter without being condensed at the first membrane filter.

For example, a portion of the gas supply channel between the first membrane filter and the culture vessel extends in a horizontal direction. Consequently, it is possible to suppress the condensed water condensed and produced in the gas supply channel from dropping into the culture vessel.

For example, the first membrane filter is located at a lower position than a connection part of the culture vessel. Consequently, it is possible to suppress the condensed water condensed and produced in the gas supply channel from dropping into the culture vessel.

For example, the culture device includes a second membrane filter that is provided in a gas discharge channel that connects an interior of the culture vessel and outside air, and disposed in a state where a normal line of a filter surface is tilted with respect to a vertical direction. Consequently, this second membrane filter suppresses contamination of the culture solution in the culture vessel. Furthermore, the tilt suppresses condensed water from uniformly spreading over the entire filter surface of the second membrane filter, and a flow resistance from increasing.

For example, the culture device includes a fourth heater that heats the second membrane filter. In this case, a heating temperature of the fourth heater is higher than a heating temperature of the first heater. Consequently, the water vapor in the gas can pass through the second membrane filter without being condensed at the second membrane filter.

For example, a portion of the gas discharge channel between the second membrane filter and the culture vessel extends in a horizontal direction. Consequently, it is possible to suppress the condensed water condensed and produced in the gas discharge channel from dropping into the culture vessel.

For example, the second membrane filter is located at a lower position than a connection part of the culture vessel. Consequently, it is possible to suppress the condensed water condensed and produced in the gas discharge channel from dropping into the culture vessel.

For example, the culture vessel has a columnar shape including a bottom plate part, a top plate part, and a sidewall part. In this case, the culture device includes a fifth heater that heats the top plate part, and a sixth heater that heats the sidewall part, and heating temperatures of the fifth and sixth heaters are higher than the heating temperature of the second heater. Consequently, condensation is suppressed from occurring on the top plate part and the sidewall part.

For example, the culture device includes a culture solution supply unit that supplies the culture solution to the culture vessel. In this case, as an amount of the culture solution in the culture vessel supplied by the culture solution supply unit increases, a gas supply amount per unit time of the gas supply device is changed. When an amount of the culture solution in the culture vessel is large, and evaporation of the culture solution does not significantly affect cells, an excessive amount of the gas is suppressed from being supplied to the culture vessel.

For example, the gas supply amount of the gas supply device is changed such that an evaporation percentage at the culture solution amount in the culture vessel and an osmotic pressure of the culture solution calculated from the evaporation percentage take predetermined values. Consequently, it is possible to suppress the deformation of the cells due to the osmotic pressure of the culture solution.

In one example, the predetermined value of the osmotic pressure of the culture solution is in a range of 260 to 315 mOsm/kg.

For example, as the amount of the culture solution in the culture vessel supplied by the culture solution supply unit increases, the heating temperature of the first heater is changed. Consequently, when an amount of the culture solution in the culture vessel is large, and evaporation of the culture solution does not significantly affect cells, an excessive amount of the water vapor is suppressed from being supplied to the culture vessel.

For example, before the culture solution supply unit supplies the culture solution to the culture vessel, the gas supplied from the gas supply device and humidified by the humidification device is supplied to the culture vessel. Consequently, evaporation of a small amount of the culture solution immediately after the culture solution is supplied to the culture vessel is suppressed.

Hereinafter, an embodiment of the present invention will be described with reference to the drawings.

FIG. 1 is a schematic configuration diagram illustrating a configuration of a culture device according to the embodiment of the present invention.

As illustrated in FIG. 1, a culture device 10 includes a culture vessel 12 that contains a culture solution CS containing cells, a culture vessel rocking unit 14 that rocks the culture vessel 12 to stir the culture solution CS in the culture vessel 12, and a culture solution supply unit 16 that supplies the culture solution CS to the culture vessel 12.

Furthermore, in the case of the present embodiment, the culture device 10 includes a humidity sensor 18 that measures a humidity in the culture vessel 12, a dissolved oxygen sensor 20 that measures an amount of oxygen dissolved in the culture solution CS in the culture vessel 12, and a cell density measuring unit 22 that measures a cell density in the culture solution CS in the culture vessel 12.

Furthermore, the culture device 10 includes a gas supply unit 24 that supplies a humidified mixed gas of oxygen, carbon dioxide, and nitrogen to the culture vessel 12.

Furthermore, the culture device 10 includes a control unit 26 that controls the culture vessel rocking unit 14, the culture solution supply unit 16, and the gas supply unit 24 based on the respective detection results of the humidity sensor 18, the dissolved oxygen sensor 20, and the cell density measuring unit 22.

The culture vessel 12 is a vessel for containing the culture solution CS, and culture cells using the culture solution CS inside. In this culture vessel 12, as the number of cells increases, cell culture performed using the culture solution CS while adding the culture solution CS stepwise from a small amount (less than one liter such as 50 milliliters), that is, cell expansion is performed. Therefore, the culture vessel 12 has a capacity capable of containing and stirring a maximum amount (e.g., 50 liters) of a culture solution used for culture.

Figure 2:
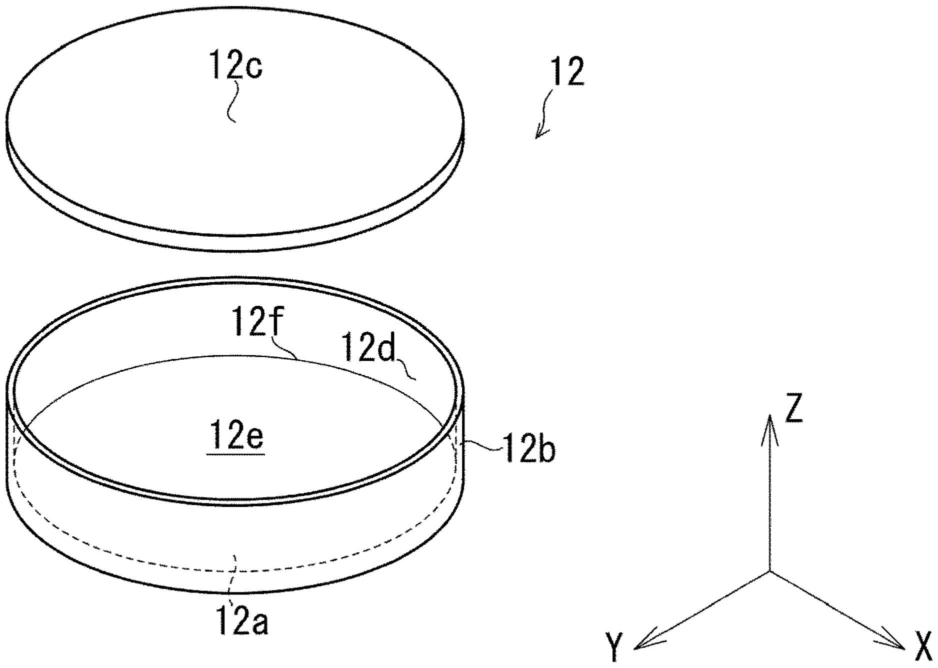
FIG. 2 is a schematic perspective view of an example of a culture vessel.

FIG. 2 is a perspective view illustrating a shape of an example of the culture vessel 12. Note that FIG. 2 illustrates an X-Y-Z orthogonal coordinate system to facilitate understanding of the embodiment of the invention, yet does not limit the invention. Furthermore, an X axis direction and a Y axis direction are horizontal directions, and a Z axis direction is a vertical direction.

As illustrated in FIG. 2, in the case of the present embodiment, the culture vessel 12 includes a disk-shaped bottom plate part 12*a*, a cylindrical sidewall part 12*b* vertically standing from an outer circumferential edge of the bottom plate part 12*a*, and a top plate part 12*c* supported by the sidewall part 12*b*. That is, the culture vessel 12 has a so-called columnar shape. A height of the sidewall part 12*b* is smaller than a radius of the bottom plate part 12*a*. Furthermore, the top plate part 12*c* is detachable and functions as a lid.

Figure 3:
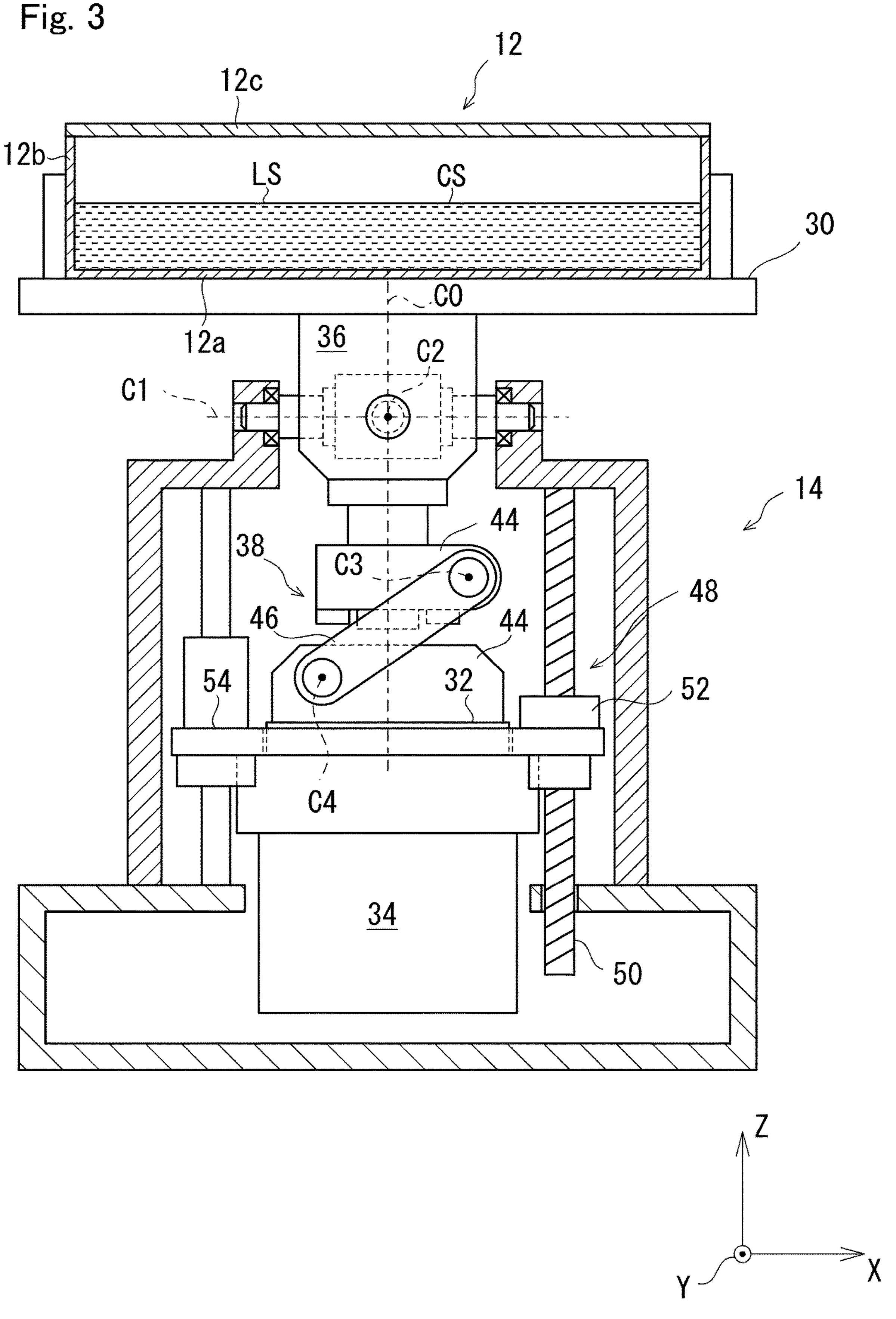
FIG. 3 is a schematic partial cross-sectional view of a culture vessel rocking unit in the culture device.

FIG. 3 is a schematic partial cross-sectional view of the culture vessel rocking unit 14 in the culture device 10. Furthermore, FIG. 4 is a schematic partial cross-sectional view of part of the culture vessel rocking unit 14 illustrated in FIG. 3 seen from a different direction.

Figure 4:
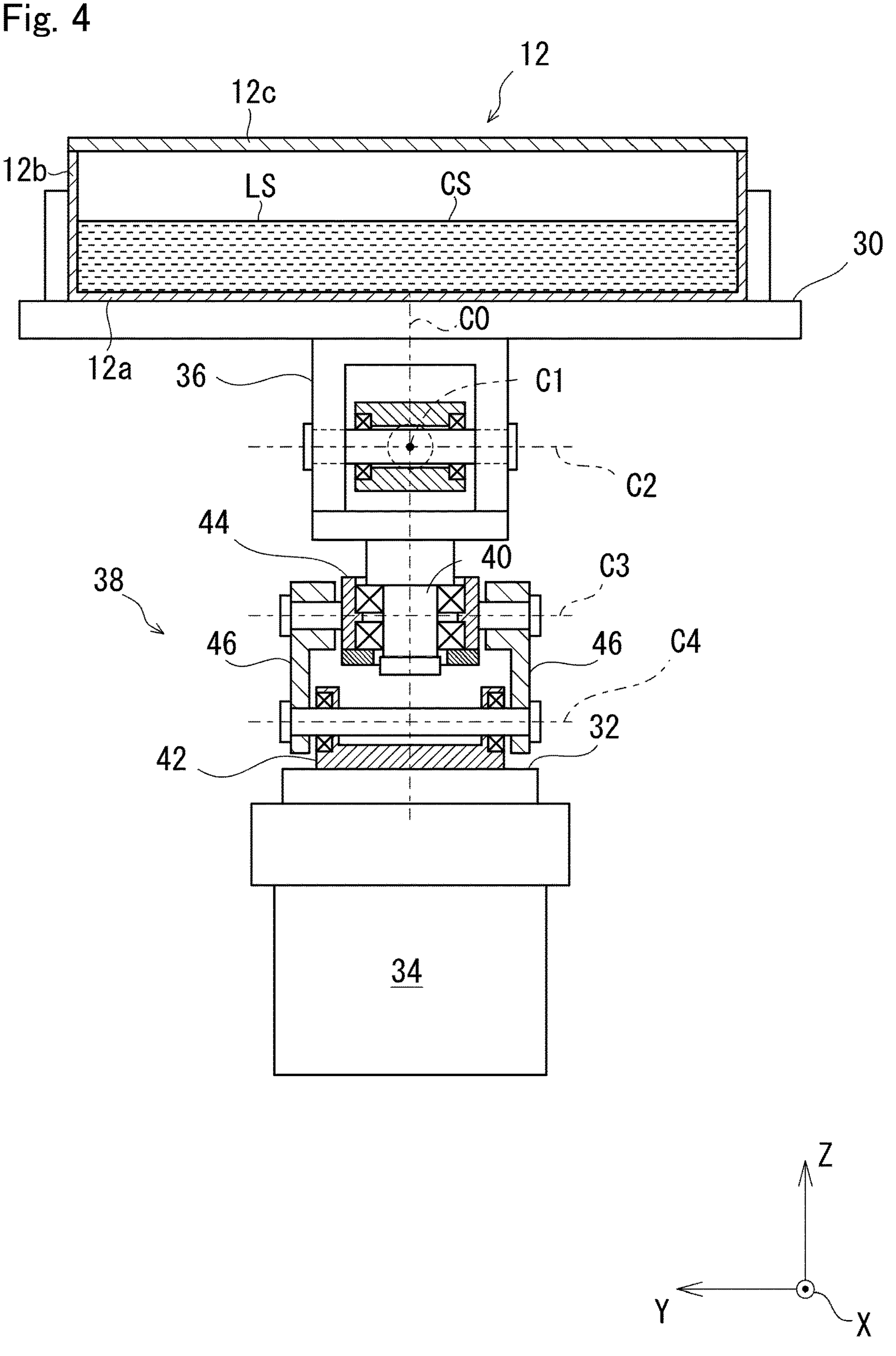
FIG. 4 is a schematic partial cross-sectional view of part of the culture vessel rocking unit illustrated in FIG. 3 seen from a different direction.

As illustrated in FIGS. 3 and 4, the culture vessel rocking unit 14 in the culture device 10 includes a stage 30 that holds the culture vessel 12, and a rotary actuator 34 that includes a rotary table 32 that rotates about a rotation center axis C0 extending in the vertical direction (Z axis direction).

The stage 30 and the rotary actuator 34 are drivingly coupled with a rocking head 36 and a tilting mechanism 38 interposed therebetween.

The rocking head 36 is provided on the culture vessel rocking unit 14 so as to support the stage 30, and be swingable about a rocking axis C1 extending in the horizontal direction (X axis direction) and a rocking axis C2 extending in the horizontal direction (Y axis direction) and orthogonal to the rocking axis C1. Furthermore, the rocking head 36 includes at a lower portion a coupling shaft 40 for drivingly coupling with the rotary actuator 34 with the tilting mechanism 38 interposed therebetween. When the stage 30 takes a horizontal posture, the coupling shaft 40 of the rocking head 36 extends in the vertical direction (Z axis direction).

The tilting mechanism 38 is a link mechanism for tilting the stage 30 via the rocking head 36, that is, for tilting the culture vessel 12 on the stage 30 with respect to the horizontal direction. To perform tilting, the tilting mechanism 38 includes a base part 42, rocking head coupling parts 44 that are coupled to the rocking head 36, and link arms 46 that couple the base part 42 and the rocking head coupling parts 44.

The base part 42 of the tilting mechanism 38 is attached to the rotary table 32 of the rotary actuator 34. Therefore, when the rotary actuator 34 is driven, the base part 42 rotates about the rotation center axis C0 together with the rotary table 32.

The rocking head coupling parts 44 of the tilting mechanism 38 are slidably fitted onto the coupling shaft 40 of the rocking head 36 with, for example, bearings interposed therebetween.

The link arms 46 of the tilting mechanism 38 are configured to couple the base part 42 and the rocking head coupling parts 44. Specifically, the link arm 46 includes one end pivotally fixed to the rocking head coupling part 44, and an other end pivotally fixed to the base part 42. A pivot axis C3 at one end and a rotation axis C4 at the other end of the link arm 46 extend in the horizontal direction and are parallel to each other.

The rotary actuator 34 to which the base part 42 of the tilting mechanism 38 is attached is raised and lowered in the vertical direction (Z axis direction) by a ball screw mechanism 48.

The ball screw mechanism 48 includes a screw shaft 50 that extends in the vertical direction (Z axis direction), a nut 52 that engages with the screw shaft 50, and a motor (not illustrated) that rotates the screw shaft 50. The nut 52 is attached to a lifting bracket 54. The rotary actuator 34 is attached to this lifting bracket 54.

Figure 5:
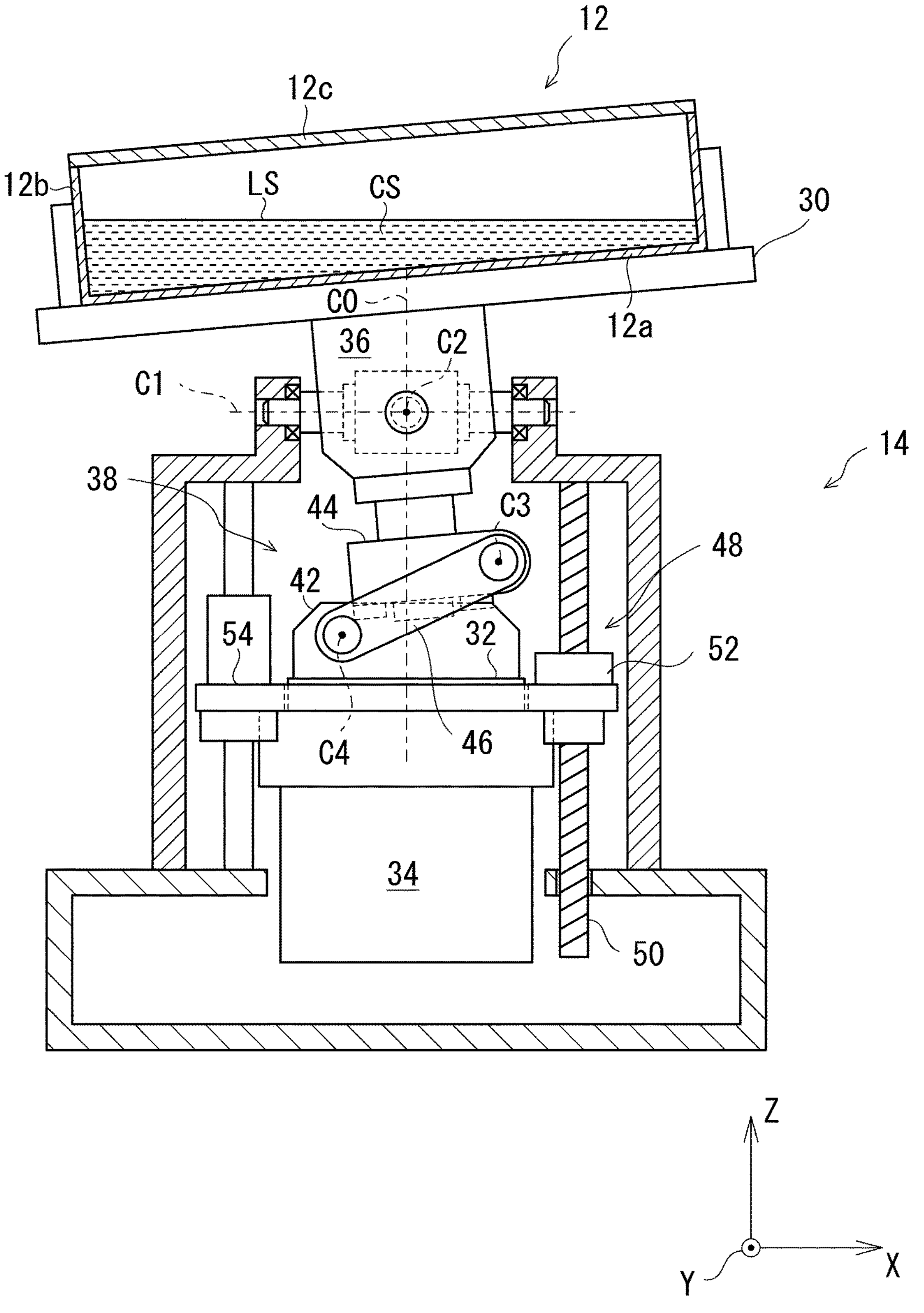
FIG. 5 is a schematic partial cross-sectional view of the culture vessel rocking unit illustrated in FIG. 3 in a state where the culture vessel is tilted.

When the ball screw mechanism 48 is driven, the rotary actuator 34 is raised and lowered together with the lifting bracket 54 via the nut 52. For example, as illustrated in FIG. 5, when the rotary actuator 34 is raised by the ball screw mechanism 48, the stage 30 is tilted via the tilting mechanism 38. More specifically, the base part 42 of the tilting mechanism 38 attached to the rotary actuator 34 rises, and thereby the link arms 46 push the rocking head coupling parts 44. As a result, the rocking head 36 rotates about at least one of the rocking axes C1 and C2 (the rocking axis C2 in FIG. 5) together with the rocking head coupling parts 44. As a result, the stage 30 is tilted, and the culture vessel 12 on this stage 30 is also tilted.

When the rotary actuator 34 is driven and the rotary table 32 rotates in a state where the stage 30 is tilted as illustrated in FIG. 5, the tilting mechanism 38 rotates about the rotation center axis C0, and thereby a tilting direction of the stage 30 changes. As a result, the culture solution CS in the culture vessel 12 is stirred, and the cells in the culture solution CS are cultured.

Note that, even when the rotary actuator 34 rotates the tilting mechanism 38 once, for example, in this culture vessel rocking unit 14, the stage 30 itself does not rotate, and the tilting direction of the stage 30 only rotates once instead. That is, a lowest portion of the culture vessel 12 on the stage 30 is only sequentially changed to another portion.

Back to FIG. 1, in the case of the present embodiment, the culture solution supply unit 16 that supplies the culture solution CS to the culture vessel 12 is controlled by the control unit 26. Supply of the culture solution CS to the culture vessel 12 will be described later.

Furthermore, in addition to the culture solution CS, a mixed gas is supplied to the culture vessel 12 by the gas supply unit 24. Supply of the gas to the culture vessel 12 will be described later.

The humidity sensor 18 is attached in the culture vessel 12 and, more specifically, to an inner circumferential surface 12*d* so as not to be immersed in the culture solution CS, and measures the humidity in the culture vessel 12. Furthermore, the humidity sensor 18 outputs a signal corresponding to the measured humidity to the control unit 26.

The dissolved oxygen sensor 20 measures an amount of oxygen dissolved in the culture solution CS in the culture vessel 12. For example, a fluorescent dissolved oxygen sensor is used as the dissolved oxygen sensor 20. For example, the fluorescent dissolved oxygen sensor includes a chip disposed on a bottom surface 12*e* of the culture vessel 12 and coated with a fluorescent substance, a light source that irradiates the chip with ultraviolet light or the like from an outside of the culture vessel 12, and a light receiving element that receives fluorescence emitted from the chip.

When the fluorescent substance absorbs light energy such as ultraviolet light from the light source, a ground state transitions to an excited state. Molecules of the excited fluorescent substance usually radiate fluorescence, and return to the ground state. However, at this time, when oxygen molecules exist around the molecules in the excited state, so-called oxygen quenching where excitation energy is deprived by the oxygen molecules, and a radiant intensity of the fluorescence decreases occurs. By utilizing this oxygen quenching, that is, by utilizing the fact that the radiant intensity of the fluorescence is inversely proportional to an oxygen molecular concentration, the fluorescent dissolved oxygen sensor measures a dissolved oxygen amount in the culture solution in the culture vessel.

Furthermore, the dissolved oxygen sensor 20 outputs a signal corresponding to the measured dissolved oxygen amount to the control unit 26.

The cell density measuring unit 22 measures the cell density of the culture solution CS in the culture vessel 12. This measured cell density is output to the control unit 26. The cell density during culture is monitored by periodic measurement of the cell density measuring unit 22.

The control unit 26 includes, for example, a control board on which a storage device and a CPU are mounted. By operating according to a program stored in the storage device, the CPU executes an operation related to cell culture described later.

First, the control unit 26 controls the culture solution supply unit 16.

The culture solution supply unit 16 is controlled by the control unit 26 to additionally supply the culture solution CS to the culture vessel 12 as the number of cells in the culture solution CS in the culture vessel 12 increases. Until, for example, the amount of the culture solution CS of less than one liter (e.g., 200 milliliters) reaches 50 liters in one culture vessel 12, the culture solution CS is additionally supplied stepwise to the culture vessel 12.

Furthermore, the control unit 26 controls the culture vessel rocking unit 14 (the rotary actuator 34 and the ball screw mechanism 48 thereof) based on the amount of the culture solution CS in the culture vessel 12.

The culture vessel rocking unit 14 is controlled by the control of the control unit 26 to rock the culture vessel 12 such that the culture solution CS is stirred while evaporation of this culture solution CS in the culture vessel 12 is suppressed. More specifically, the culture vessel rocking unit 14 rocks the culture vessel 12 such that, when the amount of the culture solution CS in the culture vessel 12 becomes smaller, a portion of the surface of the culture vessel 12 brought into contact with the culture solution moved by stirring becomes smaller. This rocking of the culture vessel 12, that is, stirring of the culture solution CS will be described.

Figure 6A:
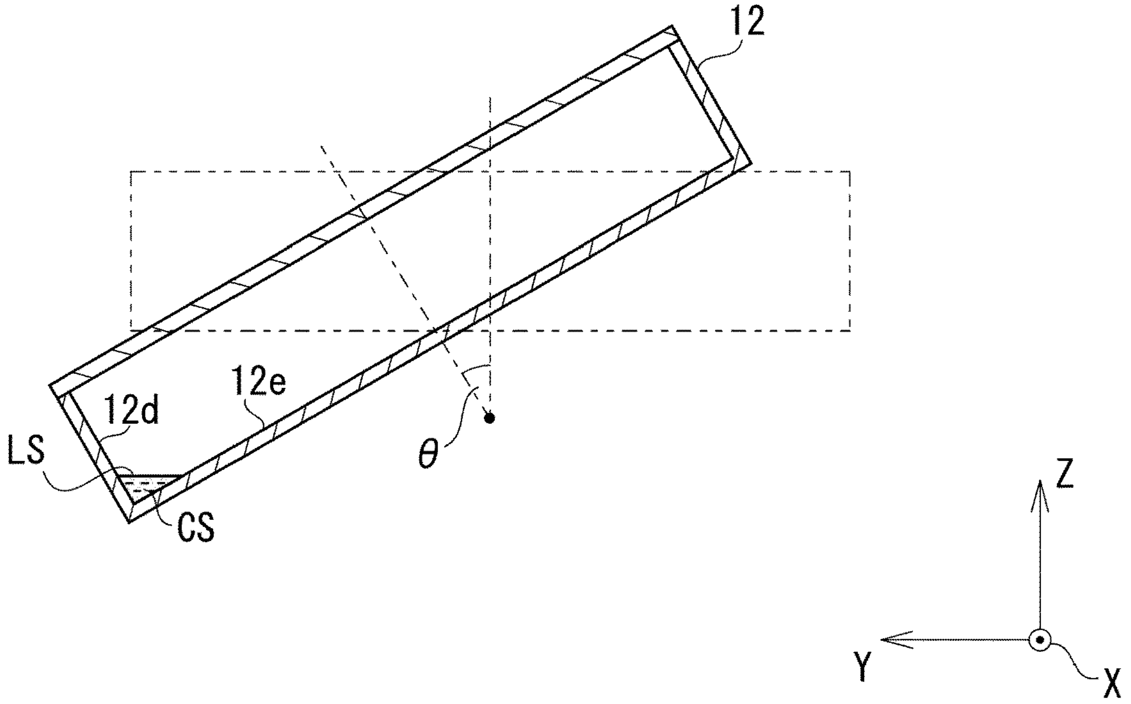
FIG. 6A is a cross-sectional view illustrating a tilted state of the culture vessel when an amount of a culture solution is relatively small.

FIG. 6A is a cross-sectional view illustrating a tilted state of the culture vessel 12 when an amount of the culture solution is relatively small. Furthermore, FIG. 6B is a top view illustrating a tilted state of the culture vessel 12 when the amount of the culture solution is relatively small.

Figure 6B:
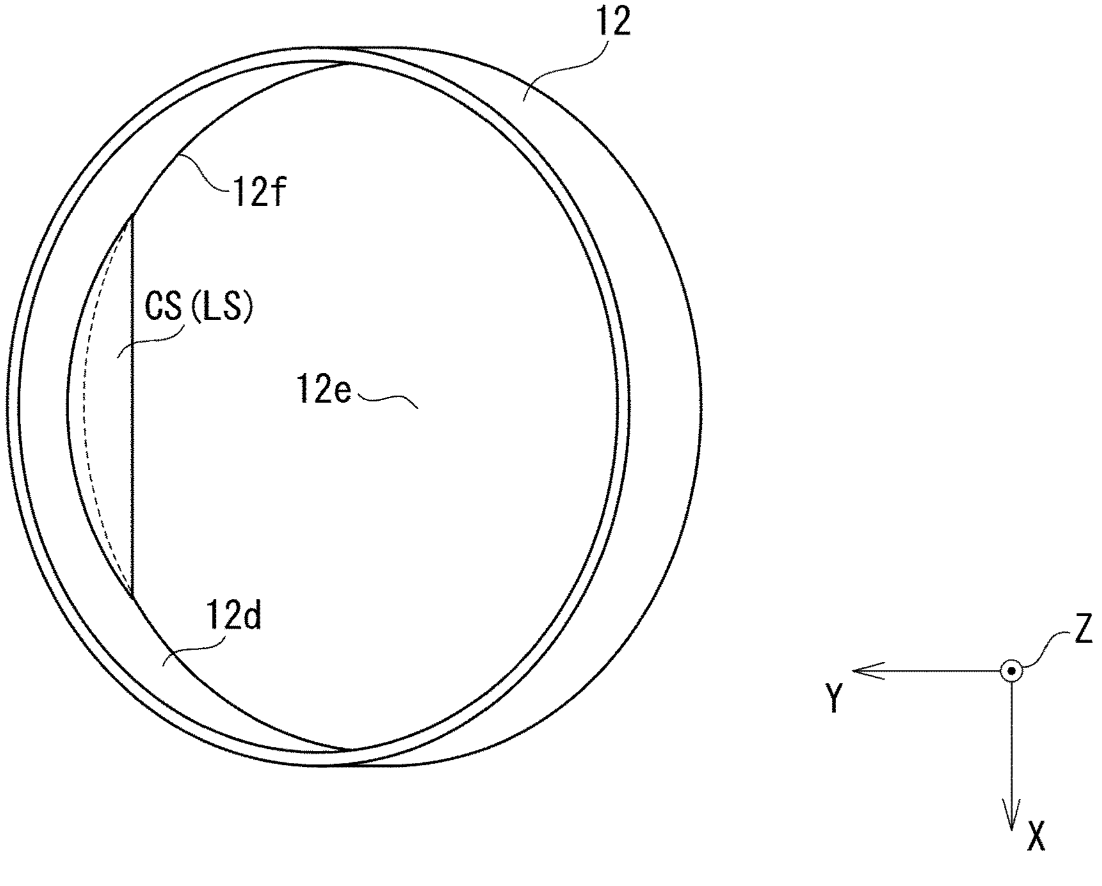
FIG. 6B is a top view illustrating a tilted state of the culture vessel when the amount of the culture solution is relatively small.

As illustrated in FIGS. 6A and 6B, the culture solution is stirred in a state where the culture vessel 12 is tilted. A tilting angle θ (an angle with respect to the culture vessel 12 in a horizontal state) of this culture vessel 12 is set larger when the amount of the culture solution CS in the culture vessel 12 is smaller.

As described above, by tilting the culture vessel 12 more greatly when the amount of the culture solution CS is smaller, a size of an area of a liquid surface LS of the culture solution CS becomes smaller. When the size of the area of the liquid surface LS becomes smaller, it is possible to suppress evaporation of the culture solution CS from this liquid surface LS.

Hereinafter, the "evaporation of the culture solution" will be described. When the culture solution CS evaporates, the cell density in the culture solution CS increases. When the amount of the culture solution CS is large (e.g., one liter or more), the amount of increase in cell density due to evaporation of the culture solution CS is relatively small, and the influence of the increase in density on the cells is little. On the other hand, when the amount of the culture solution CS is small (e.g., less than one liter), the amount of increase in cell density due to evaporation of the culture solution CS is relatively large, and the influence of the increase in density on the cells is great. When the amount of the culture solution CS is smaller, an influence of this evaporation on cells is greater, and part of the cells are killed or damaged depending on cases.

Therefore, when the amount of the culture solution CS is smaller, the culture vessel 12 is tilted greatly (by making the tilting angle θ greater) to reduce the influence of evaporation of the culture solution CS on the cells.

Note that, when the amount of the culture solution CS in the culture vessel 12 is equal to or more than such an amount or more that the influence of evaporation of the culture solution CS on the cells is sufficiently little, the tilting angle θ of the culture vessel 12 may be fixed.

When the culture vessel 12 is tilted, as illustrated in FIG. 6B, the culture solution CS is accumulated at a corner 12*f* sandwiched between a circular bottom surface 12*e* of the culture vessel 12, and the cylindrical inner circumferential surface 12*d* vertically standing from the outer circumferential edge of the bottom surface 12*e*. In this state, the tilting direction of the culture vessel 12 is changed.

Figure 7:
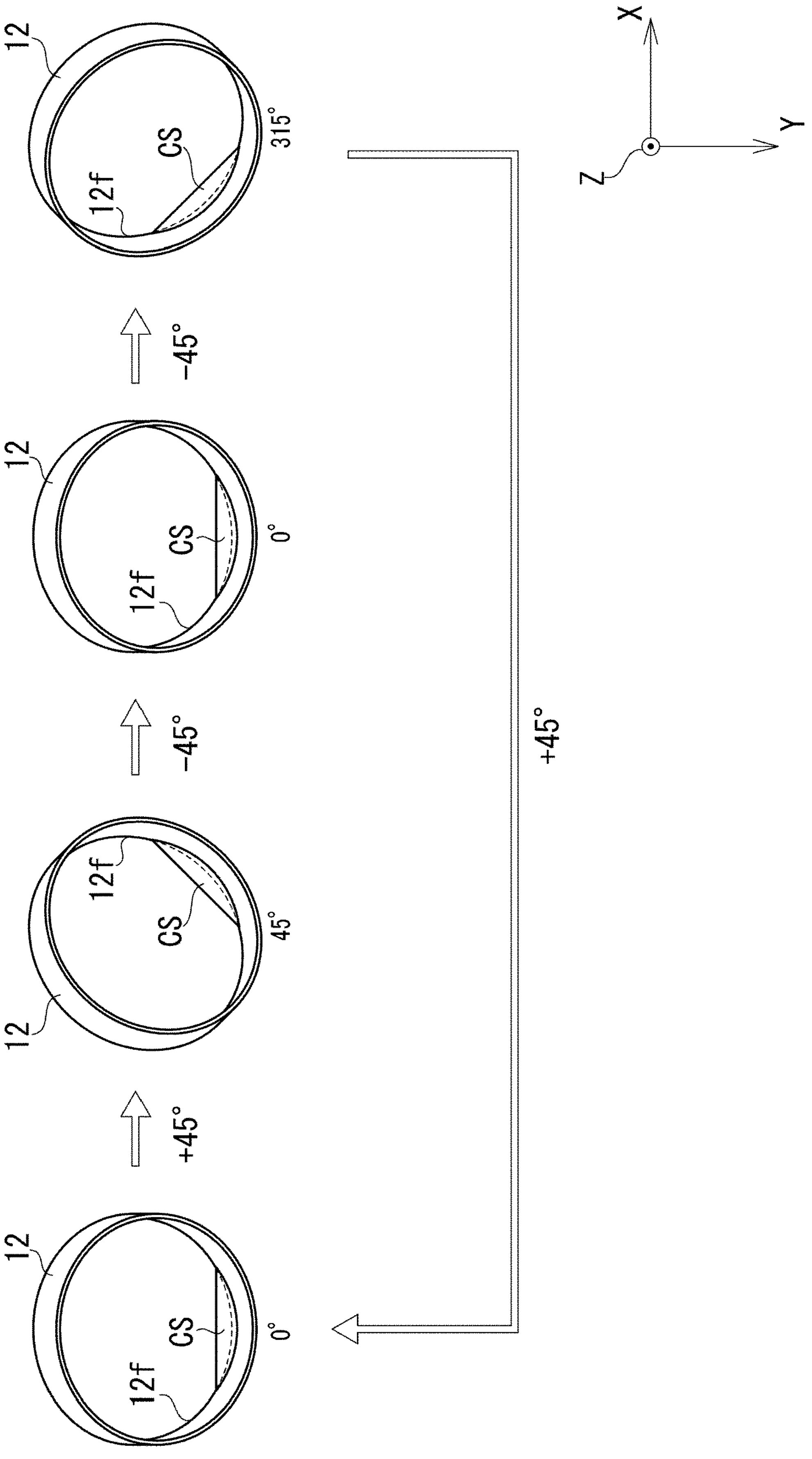
FIG. 7 is a view illustrating stirring of a culture solution when the amount of the culture solution is relatively small.

FIG. 7 is a view illustrating stirring of the culture solution when the amount of the culture solution is relatively small. FIG. 7 illustrates a state of the culture vessel 12 during stirring seen from above (seen from the Z axis direction).

As illustrated in FIG. 7, the culture solution CS of a relatively small amount (e.g., less than one liter) is moved back and forth along the corner 12*f* sandwiched between the bottom surface 12*e* and the inner circumferential surface 12*d* of the culture vessel 12. When, for example, the rotary actuator 34 repeats forward rotation and reverse rotation of the tilting mechanism 38 in an angle range of 90 degrees, the tilting direction of the culture vessel 12 changes in the angle range of 90 degrees. Thereby, the culture solution CS is moved back and forth in the angle range of 90 degrees. As a result, the culture solution CS is stirred. Note that, when a Y axis plus direction is set to a 0 degree direction with the Z axis arranged as a reference axis as illustrated in FIG. 7, for example, the culture solution CS is moved back and forth between a position of −45 degrees (315 degrees) and a position of +45 degrees with the position of 0 degree arranged as the center.

When the amount of the culture solution CS is smaller, a back-and-forth movement range (angle range) of the culture solution CS is set smaller. A reason for this is to suppress evaporation of the culture solution CS.

More specifically, when stirring moves the culture solution CS on the surface of the culture vessel 12, a minute amount of the culture solution CS remains on the surface after most (mass) of the culture solution CS passes. For example, after the most (mass) of the culture solution CS moves to the position of 45 degrees as illustrated in FIG. 7, a minute amount of the culture solution CS remains at the position of 0 degrees. This remaining minute amount of the culture solution CS readily evaporates. Therefore, before the minute amount of this culture solution CS evaporates, the massive culture solution CS returns and absorbs the minute amount of this culture solution CS. Furthermore, when the amount of the culture solution CS is smaller, the influence of evaporation on the cells is greater, and therefore the back-and-forth movement range of the culture solution CS is reduced. Consequently, when the amount of the culture solution CS is relatively small, it is possible to suppress evaporation of the culture solution CS.

Note that, as the number of cells increases, the culture solution CS is added to the culture vessel 12, and the amount of the culture solution CS in the culture vessel 12 increases. As the amount of the culture solution CS increases, the back-and-forth movement range of the culture solution CS is expanded. This is because, while the increase in the culture solution CS reduces the influence of the evaporation on the cells, it is necessary to further stir the culture solution CS.

When the amount of the culture solution CS is relatively small (e.g., less than one liter), the culture solution CS is moved back and forth in the culture vessel 12 to suppress evaporation as described above. By contrast with this, when the culture solution CS is added as the number of cells increases, and the amount of the culture solution CS is relatively large (e.g., one liter or more), the culture solution CS is circulated in the culture vessel 12.

Figure 8A:
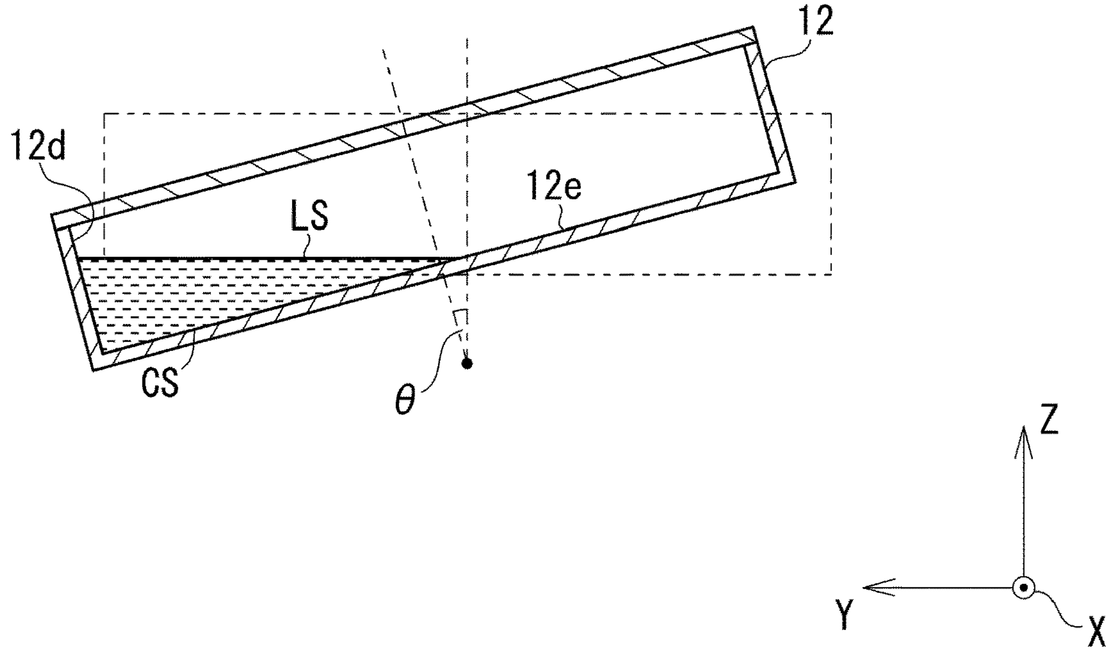
FIG. 8A is a cross-sectional view illustrating the tilted state of the culture vessel when the amount of the culture solution is relatively large.

FIG. 8A is a cross-sectional view illustrating a tilted state of the culture vessel 12 when the amount of the culture solution is relatively small. Furthermore, FIG. 8B is a top view illustrating a tilted state of the culture vessel 12 when the amount of the culture solution is relatively small.

Figure 8B:
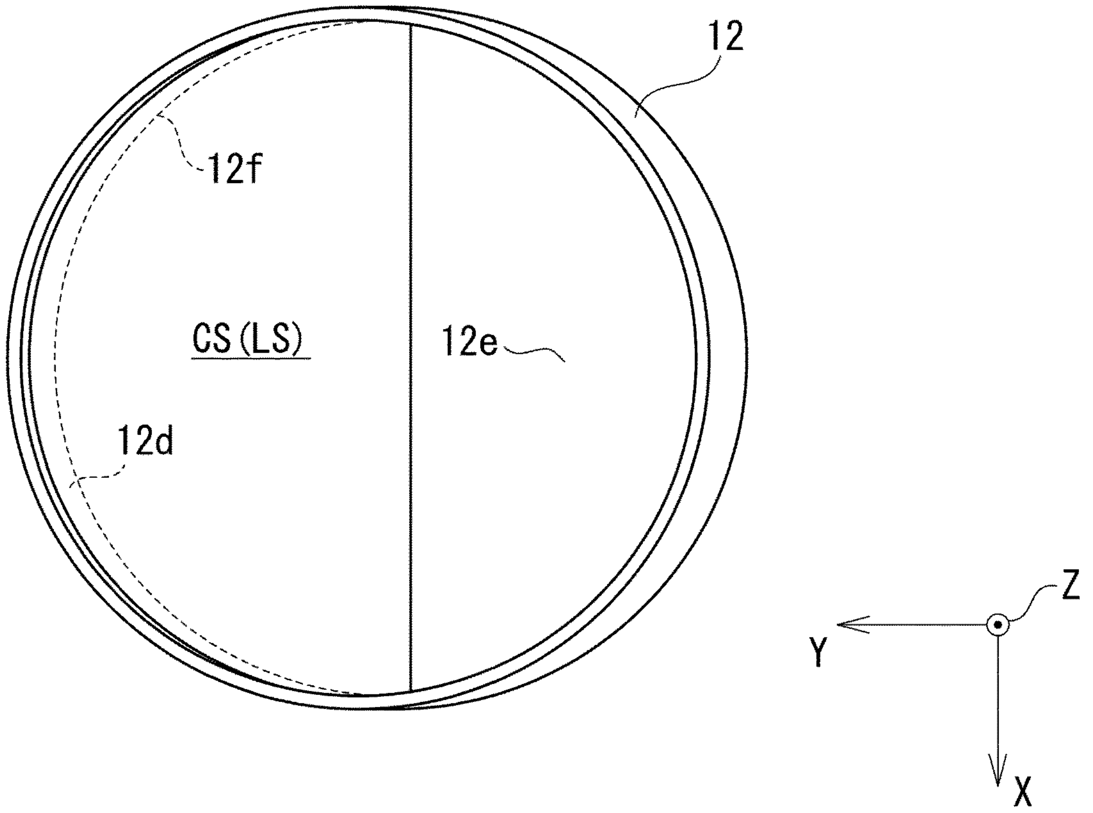
FIG. 8B is a top view illustrating the tilted state of the culture vessel when the amount of the culture solution is relatively large.

As illustrated in FIGS. 8A and 8B and in view of FIGS. 6A and 6B, the tilting angle θ of the culture vessel 12 is smaller in the case where the amount of the culture solution CS is relatively large than in the case where the amount of the culture solution CS is relatively small. This is because a depth of the culture solution CS is reduced to spread a gas such as oxygen throughout the culture solution CS.

As the depth of the culture solution CS increases, a gas such as oxygen taken in through the liquid surface of the culture solution CS by stirring hardly spreads throughout the culture solution CS. More specifically, the gas hardly reaches a deep portion of the culture solution CS. As a result, the amount of dissolved oxygen at the deep portion of the culture solution CS is insufficient, and the cells are likely to be damaged.

When the culture vessel 12 is tilted, the culture solution CS is accumulated at the corner 12*f* sandwiched between the bottom surface 12*e* and the inner circumferential surface 12*d* of the culture vessel 12 as illustrated in FIG. 8B. In this state, the tilting direction of the culture vessel 12 is changed.

Figure 9:
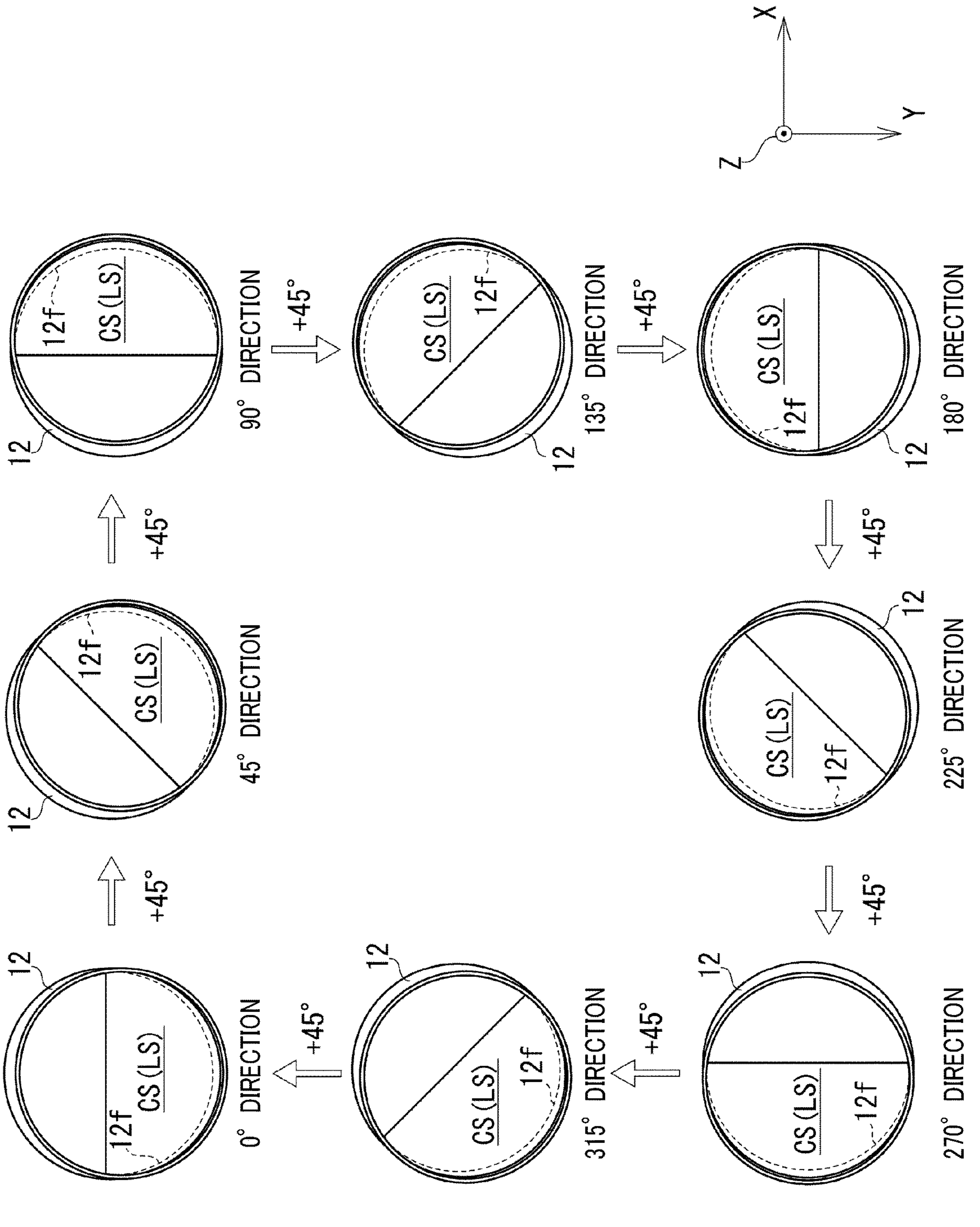
FIG. 9 is a view illustrating stirring of the culture solution when the amount of the culture solution is relatively large.

FIG. 9 is a view illustrating stirring of the culture solution CS when the amount of the culture solution CS is relatively large. FIG. 9 illustrates a state of the culture vessel 12 during stirring seen from above (seen from the Z axis direction).

The relatively large amount (e.g., one liter or more) of the culture solution CS is circulated along the corner 12*f* sandwiched between the bottom surface 12*e* and the inner circumferential surface 12*d* of the culture vessel 12. For example, the rotary actuator 34 continues to rotate the tilting mechanism 38 in one direction, so that the tilting direction of the culture vessel 12 continues to rotate in one direction. Thus, the culture solution CS is circulated. As a result, the culture solution CS is stirred.

In this way, the control unit 26 changes a stirring mode (rocking pattern) based on the amount of the culture solution CS in the culture vessel 12. When, for example, the amount of the culture solution CS in the culture vessel 12 is smaller than a predetermined threshold amount (e.g., one liter), the culture solution CS is stirred by moving the culture solution CS back and forth as illustrated in FIG. 7. Furthermore, when the amount of the culture solution CS is smaller, the back-and-forth movement range of this culture solution CS is made smaller. On the other hand, when the amount of the culture solution CS in the culture vessel 12 exceeds the predetermined threshold amount, the culture solution CS is circulated to stir this culture solution CS as illustrated in FIG. 9. Note that the amount of the culture solution CS in the culture vessel 12 may be calculated from, for example, a weight of the culture solution CS in the culture vessel 12 measured by a weight sensor (not illustrated).

In addition, in the case of the present embodiment, the control unit 26 is configured to control the culture vessel rocking unit 14 based on measurement results of the humidity sensor 18 and the dissolved oxygen sensor during stirring of the culture solution CS.

More specifically, when the humidity in the culture solution CS detected by the humidity sensor 18 lowers, that is, when, for example, the humidity lowers exceeding a lower limit value of a predetermined appropriate range, the culture vessel rocking unit 14 controlled by the control unit 26 increases the tilting angle of the culture vessel 12 (i.e., the stage 30) such that the area of the liquid surface LS of the culture solution CS decreases.

When the humidity in the culture vessel 12 lowers, the culture solution CS readily evaporates from the liquid surface LS thereof. Consequently, by reducing the area of the liquid surface LS of the culture solution CS, it is possible to suppress evaporation of the culture solution CS.

Furthermore, when the amount of dissolved oxygen detected by the dissolved oxygen sensor lowers, that is, when, for example, the amount of dissolved oxygen lowers exceeding a lower limit value of a predetermined appropriate range, the culture vessel rocking unit 14 controlled by the control unit 26 rocks the culture vessel 12 such that at least one of a back-and-forth movement cycle and the back-and-forth movement range of the culture solution CS increases. Note that, regardless of the amount of the culture solution CS in the culture vessel 12, the dissolved oxygen sensor 20 (the chip thereof) is provided at a position on the culture vessel 12 where the dissolved oxygen sensor 20 can contact the culture solution CS and detect the dissolved oxygen amount thereof. In the case of the present embodiment, the dissolved oxygen sensor 20 is provided at the outer circumferential edge of the bottom surface 12*e* of the culture vessel 12. Furthermore, when the dissolved oxygen sensor 20 measures the dissolved oxygen amount, the culture vessel 12 is rocked by the culture vessel rocking unit 14 such that the culture solution CS contacts this dissolved oxygen sensor 20. In this case, in order to bring the culture solution CS into contact with the dissolved oxygen sensor 20 and accurately detect the dissolved oxygen amount of the culture solution CS, a rocking speed and a rocking pattern of the culture vessel 12 may be temporarily changed, or rocking of the culture vessel 12 may be temporarily stopped.

When the amount of dissolved oxygen in the culture solution CS in the culture vessel 12 decreases, the cells in the culture solution CS are damaged. Consequently, by increasing at least one of the back-and-forth movement cycle and the back-and-forth movement range of the culture solution CS, the culture solution CS is further stirred, and thereby a large amount of oxygen is taken into the culture solution CS. As a result, it is possible to suppress damages on the cells.

Note that, when the amount of the culture solution CS in the culture vessel 12 is relatively large and the large amount of the culture solution CS is circulated, the culture solution CS is further stirred by increasing a circulation speed thereof, so that it is possible to take a large amount of oxygen into the culture solution CS.

Furthermore, in the case of the present embodiment, the control unit 26 controls the amount of gas supplied to the culture vessel 12 by the gas supply unit 24 based on the culture solution amount in the culture vessel 12. A configuration of this gas supply unit 24 will be described first.

Figure 10:
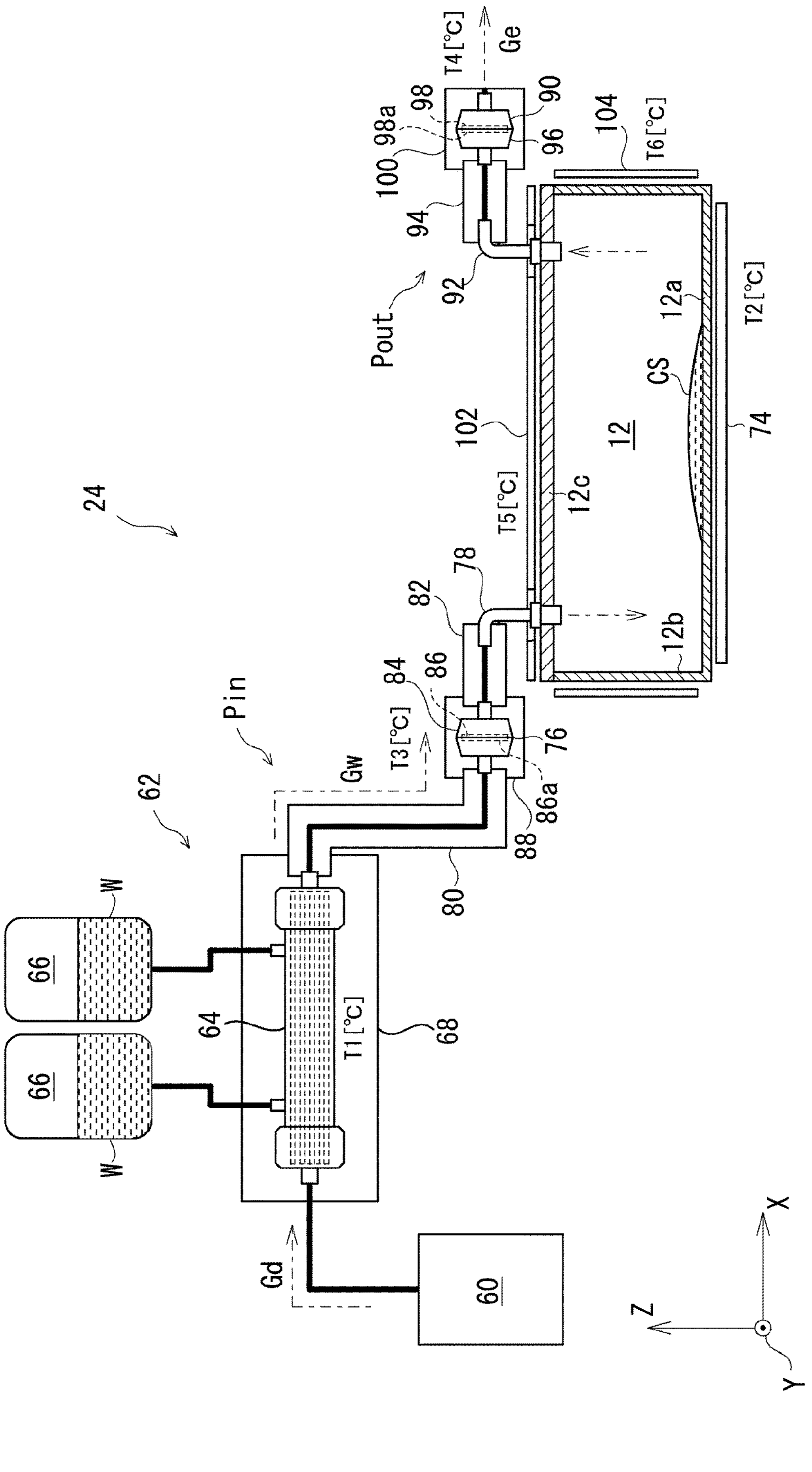
FIG. 10 is a schematic configuration diagram of a gas supply unit.

FIG. 10 is a schematic configuration diagram of the gas supply unit.

As illustrated in FIG. 10, the gas supply unit 24 includes a gas supply device 60 that supplies a mixed gas of oxygen, carbon dioxide, and nitrogen to the culture vessel 12, and a humidification device 62 that humidifies the gas flowing from the gas supply device 60 to the culture vessel 12.

The gas supply device 60 is configured to supply a predetermined supply amount of the mixed gas contained in a gas tank (not shown) at a predetermined timing based on an instruction (control signal) from the control unit 26. For example, the gas supply device 60 is a flow rate regulating valve disposed between the gas tank and the humidification device 62.

The humidification device 62 is disposed between the gas supply device 60 and the culture vessel 12. Furthermore, the humidification device 62 includes a hollow fiber membrane filter 64 through which a mixed gas Gd from the gas supply device 60 passes, a plurality of water supply devices 66 that fill the hollow fiber membrane filter 64 with water, and a first heater 68 that heats the hollow fiber membrane filter 64. In the case of the present embodiment, water supply devices 66 are two water supply containers 66.

Figure 11:
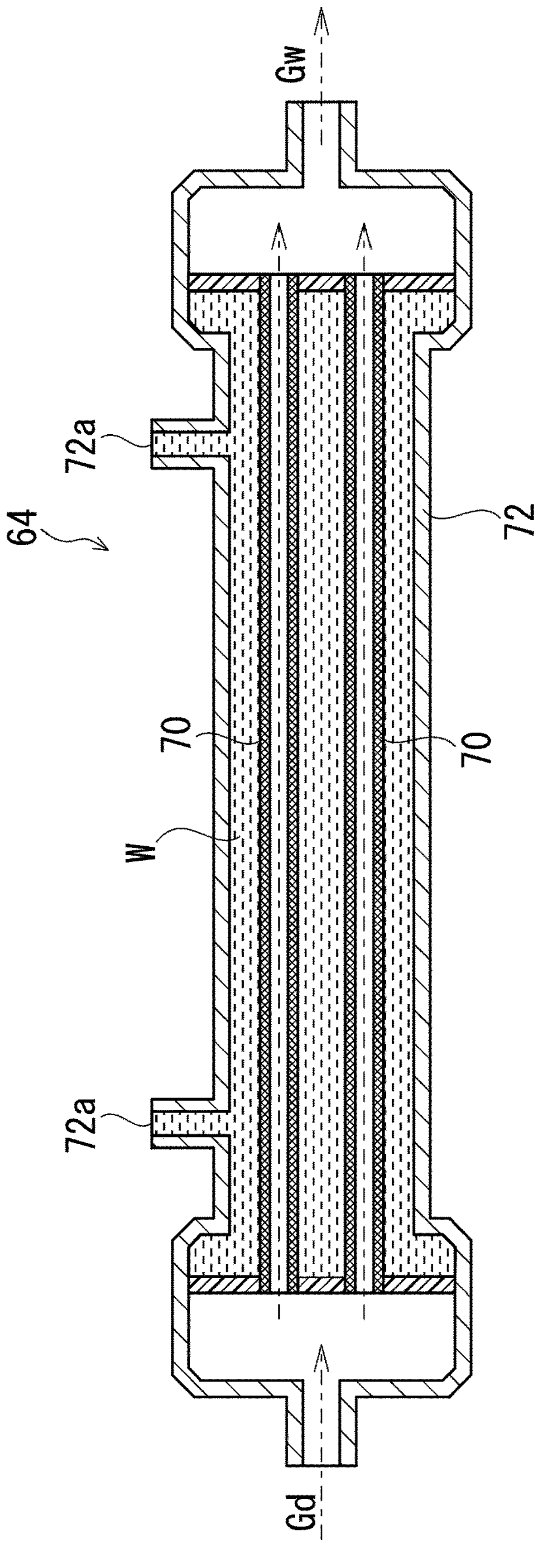
FIG. 11 is a schematic internal structural view of a hollow fiber membrane filter.

FIG. 11 is a schematic internal structural view of the hollow fiber membrane filter.

The hollow fiber membrane filter 64 includes a plurality of hollow fiber membranes 70 through which the mixed gas Gd from the gas supply device 60 passes, and a casing 72 that accommodates the plurality of hollow fiber membranes 70. The casing 72 is provided with ports 72*a* respectively connected to the two water supply containers 66. Water W in the water supply container 66 is filled in the casing 72 through the ports 72*a*. Note that the casing 72 starts being filled with the water W in a state where one of the water supply containers 66 stores the water W and the other one is empty. When the water in the one water supply container 66 that stores the water W is supplied into the casing 72, air in the casing 72 moves into the empty other water supply container 66. When water surfaces in the two water supply containers 66 finally reach the same level, the casing 72 is filled with the water.

Although the two water supply containers 66 are provided in the case of the present embodiment, the three or more water supply containers 66 may be provided in a case where the plurality of water supply containers 66 are provided. Furthermore, the water supply containers 66 are located above the hollow fiber membrane filter 64, and water is stored in the water supply containers 66 such that the water surfaces in all of the water supply containers 66 are at the same level.

Furthermore, the water supply container 66 may be configured to have a variable internal volume. That is, for example, the water supply container 66 is formed by a piston such as a syringe, formed in a bellows shape, or at least partially formed by an elastic body.

Unlike this configuration, in a case where the water supply container 66 has a fixed inner volume and is in a sealed state, there is a probability that sufficient water cannot be supplied into the casing 72. Furthermore, there is a probability that a volume change due to a vaporized gas from the supply water caused by a temperature change or the like, and an aeration gas having passed through the hollow fiber membranes cannot be absorbed.

In addition to the configuration where the water supply container 66 has the variable inner volume, there may be provided detection units (not illustrated) that detect the movement amount of the piston indicating an internal volume change amount, a deformation amount of the bellows, or a deformation amount of an elastic part of the elastic body. As a result, it is possible to suppress breakage, leakage, and the like of the water supply containers 66 that may be caused by a volume change of the water supply containers 66 due to a gas, and it is also possible to detect the amount of supply water from the water supply containers 66 to the casing 72 via these detection units. It is possible to notify an operator of a timing of refilling the supply water based on a detection result of the supply water amount, and, consequently, it is possible to prevent a humidification function from lowering due to shortage of the supply water amount.

When the mixed gas Gd passes through the hollow fiber membranes 70 in a state where the casing 72 filled with water, the mixed gas Gd passing through the hollow fiber membranes 70 is humidified by water vapor having passed through the hollow fiber membranes 70. As a result, the humidified mixed gas Gw flows out of the casing 72. Note that a pressure (water pressure) around the hollow fiber membranes 70 is set to a higher pressure than a pressure (mixed gas pressure) in the hollow fiber membranes 70 such that the water vapor moves into hollow fiber membranes 70.

A water vapor amount per unit volume contained in the humidified mixed gas Gw is determined by a heating temperature T1 [° C.] of the first heater 68 that heats the hollow fiber membrane filter 64. As the heating temperature T1 is higher, the water vapor amount contained in the humidified mixed gas Gw increases. The first heater 68 is, for example, a heater (referred to as a "silicone rubber heater" below) waterproofed by coating electric heating wires with silicone rubber.

Note that the culture device 10 according to the present embodiment is provided with a second heater 74 that is disposed below the culture vessel 12 and heats the culture solution CS inside the culture vessel 12 to maintain a predetermined temperature (e.g., about 37° C.) of the culture solution CS in the culture vessel 12. The second heater 74 is, for example, a silicone rubber heater provided on the stage 30 of the culture vessel rocking unit 14. The heating temperature T1 of the first heater 68 that heats the hollow fiber membrane filter 64 is set higher than a heating temperature T2 of the second heater 74. This setting takes into account that the water vapor in the mixed gas Gw having flown out of the humidification device 62 is condensed and decreases before reaching the culture vessel 12. That is, in order to cause the mixed gas Gd to contain a larger water vapor amount in the hollow fiber membrane filter 64 than the water vapor amount required for the culture vessel 12, the heating temperature T1 of the first heater 68 is set higher than the heating temperature T2 of the second heater 74. In an example, the heating temperature T1 is set to a temperature that is 10° C. to 15° C. higher than the heating temperature T2.

The humidified mixed gas Gw having flown out of the humidification device 62 is supplied to the culture vessel 12 via a gas supply channel Pin. The gas supply channel Pin includes a first filter unit 76, an L-shaped tube joint 78 that is provided to the top plate part 12*c* of the culture vessel 12, a flexible heat insulating tube 80 that connects the humidification device 62 and the first filter unit 76, and a flexible heat insulating tube 82 that connects the first filter unit 76 and the L-shaped tube joint 78.

The first filter unit 76 is a unit for suppressing contamination of the culture solution CS in the culture vessel 12, and includes in a housing 84 a first membrane filter 86 through which the humidified mixed gas Gw passes. In the case of the present embodiment, the first membrane filter 86 is disposed in a state where a normal line of a filter surface 86*a* through which the mixed gas Gw passes is tilted with respect to the vertical direction (Z axis direction) (a state where the normal line is tilted by 90 degrees with respect to the vertical direction in the case of the present embodiment). The reason why the first membrane filter 86 is disposed at such a posture will be described.

Condensed water produced at a portion of the gas supply channel Pin from the humidification device 62 to the first membrane filter 86 is captured by the first membrane filter 86. At this time, in a case where the normal line of the filter surface 86*a* extends in the vertical direction unlike the present embodiment, the captured condensed water uniformly spreads over the entire filter surface 86*a* of the first membrane filter 86. As a result, a flow resistance of the first membrane filter 86 increases, and the mixed gas or the water vapor of a required amount does not reach the inside of the culture vessel 12.

As a countermeasure therefor, the first membrane filter 86 is disposed such that the normal line of this filter surface 86*a* is tilted with respect to the vertical direction (Z axis direction). Thus, the captured condensed water moves to a low portion of the first membrane filter 86. As a result, the entire filter surface 86*a* is suppressed from being covered with the condensed water.

The culture device 10 according to the present embodiment is provided with a third heater 88 that heats the first filter unit 76, that is, the first membrane filter 86. The third heater 88 is, for example, a silicone rubber heater. This third heater 88 heats the first membrane filter 86 at the heating temperature T3 higher than the heating temperature T1 of the first heater 68 that heats the hollow fiber membrane filter 64. For example, the heating temperature T3 is set to a temperature that is 3° C. to 5° C. higher than the heating temperature T1. Consequently, the water vapor in the mixed gas Gw can pass through the first membrane filter 86 without being condensed at the first membrane filter 86.

In the case of the present embodiment, a portion of the gas supply channel Pin between the first membrane filter 86 and the culture vessel 12, that is, the heat insulating tube 82 extends in the horizontal direction (X axis direction). Thus, the water vapor in the mixed gas Gw having passed through the first membrane filter 86 is suppressed from condensing, and this condensed water is suppressed from dropping into the culture vessel 12 (compared to the case where this portion extends in the vertical direction (Z axis direction)). As a result, a local and rapid decrease in the concentration of the culture solution CS due to dropping of the condensed water is suppressed. When the concentration of the culture solution CS lowers in this way, osmotic pressures of cells change, and the cells can be damaged. In order to further suppress the condensed water from dropping, the first membrane filter 86 may be disposed at a lower position than a connection part between the gas supply channel Pin and the culture vessel 12, that is, a connection part between the heat insulating tube 82 and the L-shaped tube joint 78 if possible.

As illustrated in FIG. 10, a second filter unit 90 is provided on a gas discharge channel Pout, too, that connects an interior of the culture vessel 12 and outside air. The gas discharge channel Pout includes the second filter unit 90, an L-shaped tube joint 92 that is provided to the top plate part 12*c* of the culture vessel 12, and a flexible heat insulating tube 94 that connects the second filter unit 90 and the L-shaped tube joint 92.

The second filter unit 90 is a unit for suppressing contamination of the culture solution CS in the culture vessel 12, and includes in a housing 96 a second membrane filter 98 through which an exhaust gas Ge passes. In the case of the present embodiment, the second membrane filter 98 is disposed in a state where a normal line of a filter surface 98*a* through which the exhaust gas Ge passes is tilted with respect to the vertical direction (Z axis direction) (a state where the normal line is tilted by 90 degrees with respect to the vertical direction in the case of the present embodiment). Consequently, similarly to the first membrane filter 86, an increase in a flow resistance caused when the condensed water covers the entire filter surface 98*a* is suppressed. As a result, an excessive increase in the pressure in the culture vessel 12 is suppressed.

Similarly to the first filter unit 76 (first membrane filter 86), the culture device 10 according to the present embodiment is provided with a fourth heater 100 that heats the second filter unit 90, that is, the second membrane filter 98. The fourth heater 100 is a silicone rubber heater similar to the third heater 88. This fourth heater 100 heats the second membrane filter 98 at a heating temperature T4 such as the same heating temperature as the heating temperature T3 of the third heater 88 higher than the heating temperature T1 of the first heater 68 that heats the hollow fiber membrane filter 64. Consequently, the water vapor in the exhaust gas Ge can pass through the second membrane filter 98 without being condensed at the second membrane filter 98.

In the case of the present embodiment, a portion of the gas discharge channel Pout between the second membrane filter 98 and the culture vessel 12, that is, the heat insulating tube 94 extends in the horizontal direction (X axis direction). Thus, the water vapor in the exhaust gas Ge before passing through the second membrane filter 98 is suppressed from condensing, and this condensed water is suppressed from dropping into the culture vessel 12 (compared to the case where this portion extends in the vertical direction (Z axis direction)). As a result, a local and rapid decrease in the concentration of the culture solution CS due to dropping of the condensed water is suppressed. Note that, in order to further suppress the condensed water from dropping, the second membrane filter 98 may be disposed at a lower position than a connection part between the gas discharge channel Pout and the culture vessel 12, that is, a connection part between the heat insulating tube 94 and the L-shaped tube joint 92 if possible.

The culture device 10 according to the present embodiment further includes a fifth heater 102 that heats top plate part 12*c* of the columnar culture vessel 12, and a sixth heater 104 that heats the sidewall part 12*b*. The fifth and sixth heaters 102 and 104 are, for example, film heaters that are attached to an outer surface of the culture vessel 12, and are transparent heaters that use ITO electrodes or the like to make it possible to visually recognize the culture solution CS in the culture vessel 12.

The fifth and sixth heaters 102 and 104 heat the top plate part 12*c* and the sidewall part 12*b* to prevent the water vapor in the culture vessel 12 from condensing on inner surfaces of the top plate part 12*c* and the sidewall part 12*b* of the culture vessel 12. Hence, heating temperatures T5 and T6 of the fifth and sixth heaters 102 and 104 are set higher than the heating temperature T2 of the second heater 74 disposed below culture vessel 12. For example, the heating temperatures T5 and T6 are set to temperatures that are 0° C. to 5° C. higher than the heating temperature T2.

The gas supply device 60, the first heater 68, the second heater 74, the third heater 88, the fourth heater 100, the fifth heater 102, and the sixth heater 104 in the gas supply unit 24 are controlled by the control unit 26.

First, the control unit 26 controls the first heater 68, the second heater 74, the third heater 88, the fourth heater 100, the fifth heater 102, and the sixth heater 104 to perform heating at the heating temperatures T1 to T6 having the above-described correspondence. The control unit 26 controls the gas supply amount per unit time of the gas supply device 60 while maintaining the control of these heaters.

More specifically, as the amount of the culture solution CS supplied by the culture solution supply unit 16 increases, the control unit 26 lowers the gas supply amount per unit time of the gas supply device 60 stepwise or linearly. In other words, when the amount of the culture solution CS in the culture vessel 12 is smaller, the gas supply amount is larger.

When the amount of the culture solution CS in the culture vessel 12 is small as illustrated in FIGS. 6A and 6B, evaporation of this culture solution CS greatly damages the cells in the culture solution CS. On the other hand, when the amount of the culture solution CS in the culture vessel 12 is large as illustrated in FIGS. 8A and 8B, evaporation of this culture solution CS hardly affects the cells in the culture solution CS.

Therefore, when the amount of the culture solution CS in the culture vessel 12 is small, a large amount of the humidified mixed gas Gw, that is, a large amount of water vapor is supplied to the culture vessel 12 to provide a humidity environment of 95% RH or more in the culture vessel 12. Consequently, the culture solution CS hardly evaporates, which suppresses damages on the cells in the culture solution CS. On the other hand, when the amount of the culture solution CS in the culture vessel 12 is large, excessively injecting the mixed gas Gw in this state increases the pressure in the culture vessel 12, and therefore the gas supply amount is decreased. In this regard, the gas supply amount necessary for pH adjustment and the like of the culture solution CS is maintained.

Figure 12:
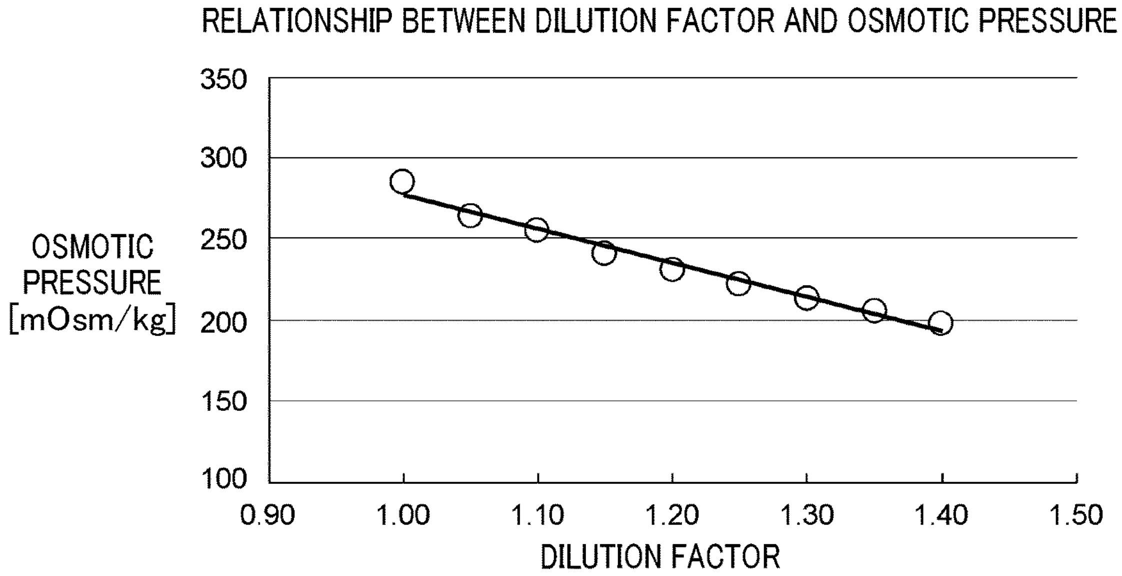
FIG. 12 is a view illustrating a dilution factor and an osmotic pressure of the culture solution.

An influence of evaporation of a culture solution on cells will be described. When the culture solution evaporates, an osmotic pressure changes and affects the cells. FIG. 12 is a view illustrating a dilution factor and an osmotic pressure in a case where an Iscove's modified Dulbecco's medium (IMDM) that is an example of a culture solution is diluted with distilled water. As illustrated in FIG. 12, as the dilution factor is increased, the osmotic pressure of the culture solution decreases. When the cells are placed in a so-called hypertonic solution having a high osmotic pressure, water in the cells goes outside, and the volume of the cells decreases. On the other hand, when the cells are placed in a so-called hypotonic solution having a low osmotic pressure, the cells draw water inside and expand. Thus, the cells are deformed and damaged by the osmotic pressure of the culture solution.

In general, an optimum osmotic pressure of a culture solution in cell culture is 265 to 315 mOsm/kg, and cells are damaged by water transfer in either a hypertonic solution or a hypotonic solution falling outside this numerical range. That is, these relationships are adjusted to achieve the optimum osmotic pressure at a dilution factor of 1.00 in the Iscove's modified Dulbecco's medium of FIG. 12, and, when the dilution factor becomes higher than the dilution factor of 1.00, the osmotic pressure decreases and, when the culture solution continues evaporating and concentrates, the osmotic pressure increases.

Figure 13:
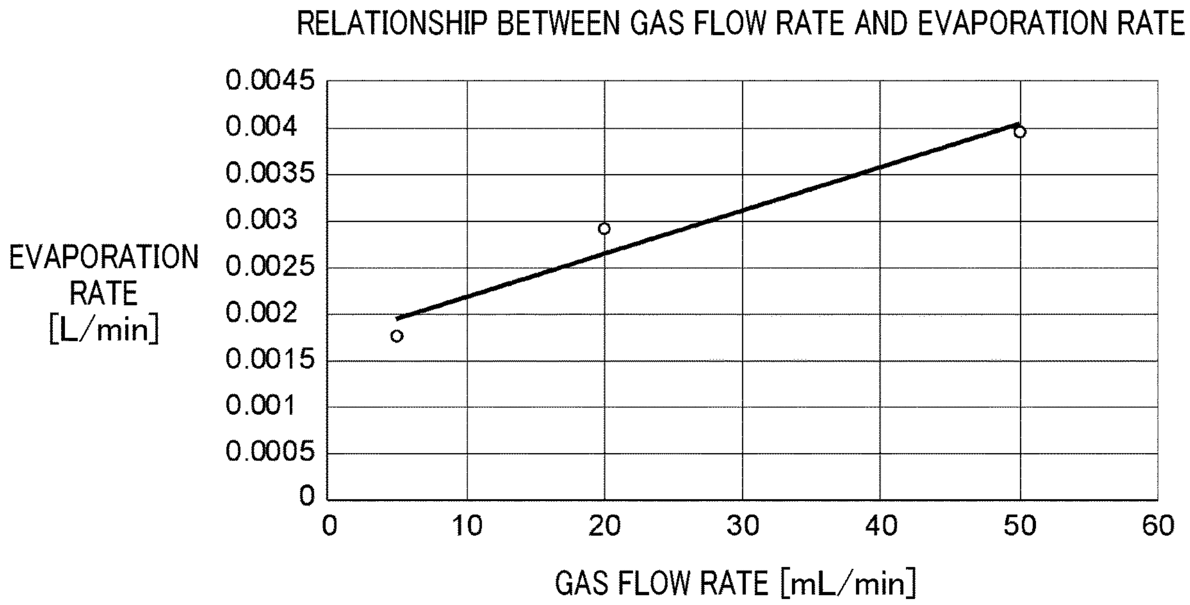
FIG. 13 is a view illustrating the relationship between a supply gas flow rate and an evaporation rate of the culture solution.

FIG. 13 is a view illustrating a result obtained by examining a gas flow rate of a mixed gas to be supplied to a culture vessel and an evaporation rate of the culture solution under a certain condition of a culture solution amount (50 ml) in the example of the present embodiment. As illustrated in FIG. 13, as the gas flow rate increases, the evaporation rate increases. Therefore, when the amount of culture solution is large, a gradient indicating the evaporation rate with respect to the gas flow rate becomes gentle, and when the amount of culture solution is small, the gradient indicating the evaporation rate with respect to the gas flow rate becomes steeper. In view of this, it is required to control the gas flow rate of the humidified mixed gas to suppress evaporation of the culture solution.

Figure 14:
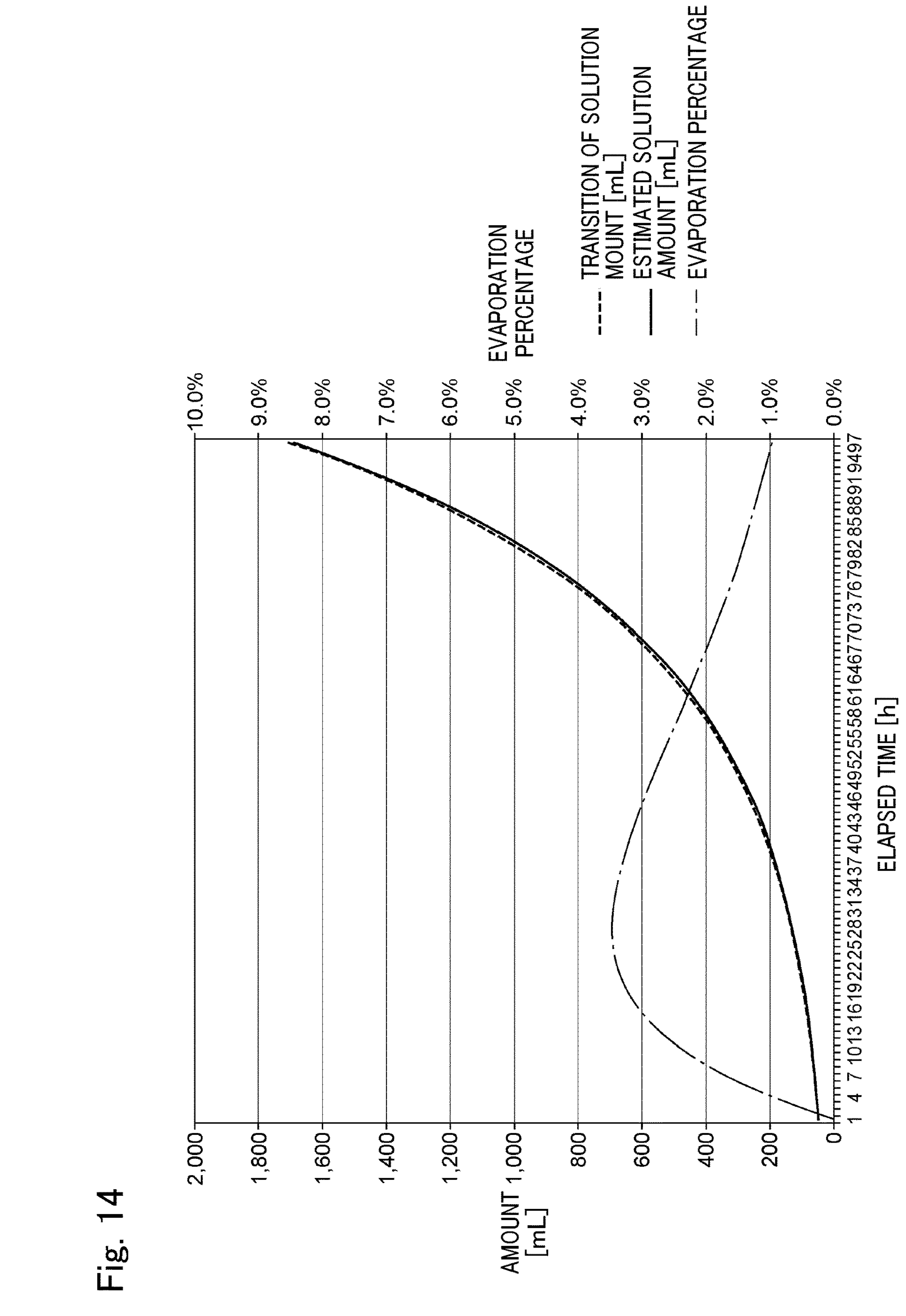
FIG. 14 is a view illustrating an amount of the culture solution and an evaporation percentage of the culture solution with respect to a culture elapsed time.

FIG. 14 is a view illustrating a culture solution amount and an evaporation percentage of the culture solution with respect to a culture elapsed time as an example of the present embodiment. A culture solution amount whose initial culture solution amount starts from 50 ml and that is the initial solution amount+an addition amount after 97 hours is indicated as an estimated solution amount (solid line) for each time. Furthermore, transition of the solution amount (broken line) that takes the evaporation rate into account is also indicated. Furthermore, FIG. 14 also illustrates transition (dashed-dotted line) of the evaporation percentage (a ratio of an evaporated solution amount to a culture solution amount) obtained from the evaporation rate at the gas flow rate in FIG. 13.

In the present embodiment, the transition of the evaporation percentage in FIG. 14 shows that the evaporation percentage takes the maximum value at a time point after the culture elapsed time passes 26 hours, and the value thereof is about 3.5%. That is, when the evaporation percentage is zero or more, the culture solution continues concentrating, an osmotic pressure increases, and acts to release water in the cells to an outside, and thereby the cells are damaged. As illustrated in FIG. 14, the evaporation percentage naturally lowers as the culture solution amount increases. In the present embodiment, the gas flow rate, the rocking conditions, and the humidity conditions are controlled such that the maximum value of the evaporation percentage is 3.5%. On the other hand, 3.5% in evaporation percentage in FIG. 14 is the same as that at 0.965 in dilution factor on the evaporation side in FIG. 12 illustrating the relationship between the dilution factor and the osmotic pressure of the culture solution, and the osmotic pressure of the culture solution can be controlled to about 290 mOsm/kg of the optimum value at this numerical value.

As described above, in the present embodiment, during cell expansion for increasing cultured cells while increasing the culture solution amount, the evaporation rate of the culture solution is controlled by controlling the flow rate of the supply gas to be supplied to the culture vessel to control evaporation of the culture solution. By this means, the osmotic pressure of the culture solution is controlled within the optimum value range to reduce damages to the cells. More specifically, the evaporation amount in a state where the culture solution amount is small is controlled to control the osmotic pressure at about 260 to 315 mOsm/kg.

In the case of the present embodiment, the control unit 26 lowers the heating temperature T1 of the first heater 68 that heats the hollow fiber membrane filter 64 as the amount of the culture solution CS supplied by the culture solution supply unit 16 increases. Consequently, the amount of water vapor contained in the mixed gas Gd decreases in the hollow fiber membrane filter 64. As a result, it is possible to reduce the amount of contained water vapor while maintaining the required amount of the mixed gas. The amount of water vapor is decreased, so that the culture solution is suppressed from being diluted. Furthermore, it is possible to suppress power consumption of the first heater 68.

Note that the heating temperature T1 of the first heater 68 may be lowered, and the heating temperature T3 of the third heater 88, the heating temperature T4 of the fourth heater 100, the heating temperature T5 of the fifth heater 102, and the heating temperature T6 of the sixth heater 104 involved in suppressing condensation may be lowered while maintaining the above-described correspondence. However, the heating temperature T2 of the second heater 74 that heats the culture solution CS in the culture vessel 12 is maintained at a required temperature regardless of the heating temperatures of the other heaters.

Furthermore, before the culture solution supply unit 16 supplies the culture solution CS to the culture vessel 12, the gas supply unit 24 may supply the humidified mixed gas Gw to the culture vessel 12. Consequently, before the culture solution CS is supplied into the culture vessel 12, the inside of the culture vessel 12 is sufficiently humidified, that is, the culture vessel 12 is filled with water vapor. As a result, evaporation of a small amount of the culture solution CS immediately after the culture solution CS is supplied to the culture vessel 12 is suppressed. Note that, in order to immediately start supplying the culture solution CS to the culture vessel 12, the maximum amount of the humidified mixed gas Gw is preferably supplied from the gas supply unit 24 to the culture vessel 12.

According to the present embodiment, it is possible to suppress evaporation of the culture solution when cells are cultured using the culture solution in the culture vessel.

Although the present invention has been described with reference to the above-described embodiment, the embodiment of the present invention is not limited to this.

For example, in the case of the above-described embodiment, as illustrated in FIG. 10, the gas supply channel Pin that supplies the humidified mixed gas Gw and the gas discharge channel Pout that discharges the exhaust gas Ge are connected to the top plate part 12*c* of the culture vessel 12. However, the embodiment of the present invention is not limited to this.

Figure 15:
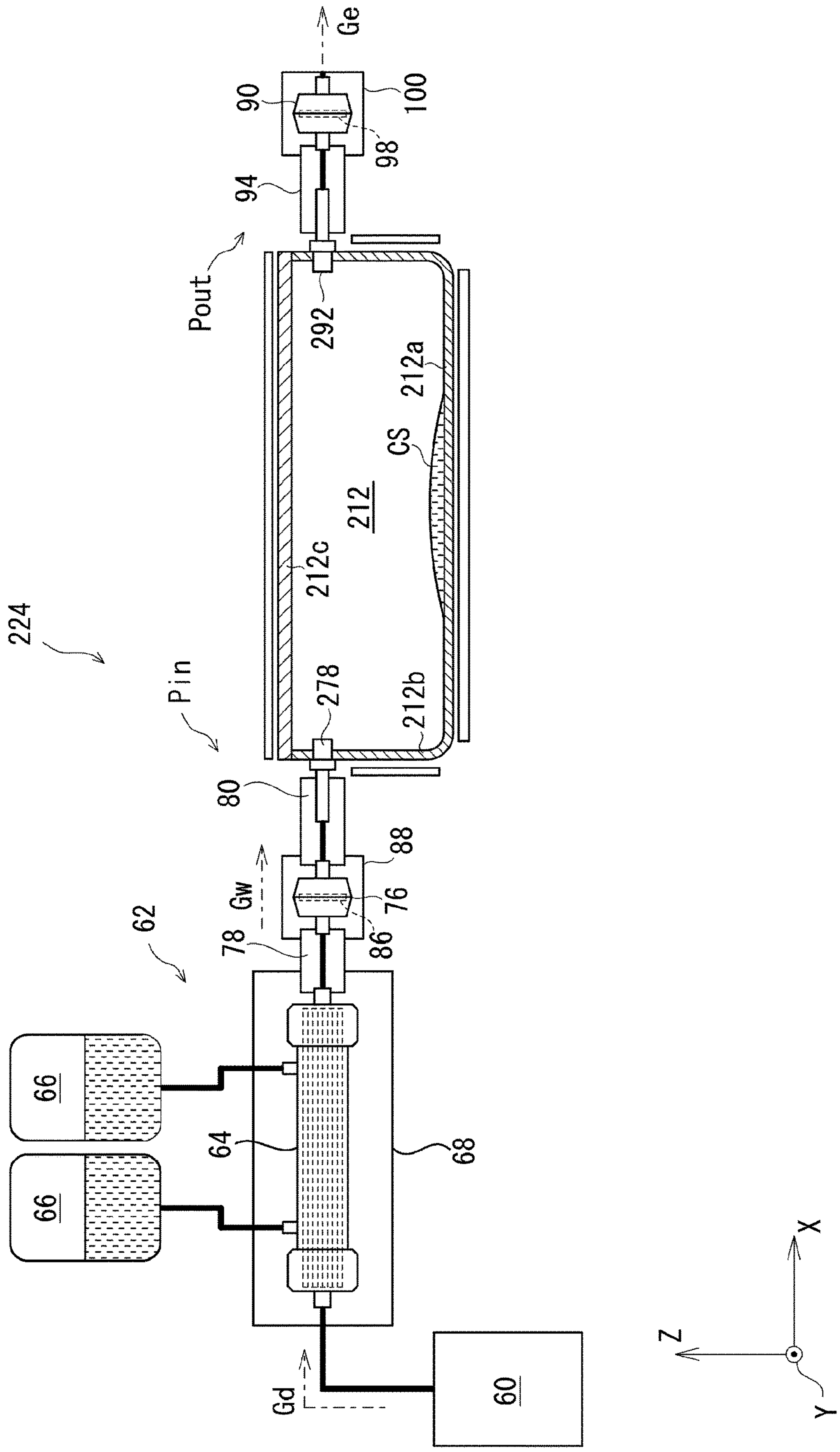
FIG. 15 is a schematic configuration diagram of the gas supply unit in a culture device according to another embodiment.

FIG. 15 is a schematic configuration diagram of the gas supply unit in a culture device according to another embodiment.

As illustrated in FIG. 15, in a gas supply unit 224 in the culture device according to another embodiment, the gas supply channel Pin that supplies a humidified mixed gas Gw is connected to a sidewall part 212*b* of a cylindrical culture vessel 212 via a straight tube joint 278 interposed therebetween. Accordingly, the entire gas supply channel Pin including the first filter unit 76, the heat insulating tubes 80 and 82, and the tube joint 278 extends in the horizontal direction (X axis direction). As a result, the condensed water is suppressed from dropping from the gas supply channel Pin to the culture vessel 212.

Similarly, the gas discharge channel Pout that discharges the exhaust gas Ge is also connected to the sidewall part 212*b* of the culture vessel 212 with a straight tube joint 292 interposed therebetween. Accordingly, the entire gas discharge channel Pout including the second filter unit 90, the heat insulating tube 94, and the tube joint 292 extends in the horizontal direction (X axis direction). As a result, the condensed water is suppressed from dropping from the gas discharge channel Pout to the culture vessel 212.

Furthermore, although the humidification device 62 humidifies the mixed gas in the gas supply unit 24 in the case of the above-described embodiment, the embodiment of the present invention is not limited to this. The humidification device may humidify a single gas such as oxygen or carbon dioxide required for culture.

Furthermore, in the case of the above-described embodiment, the culture vessel has a cylindrical shape as illustrated in FIG. 2. However, the embodiment of the present invention is not limited to this. The culture vessel may be, for example, a large Erlenmeyer flask. Furthermore, the culture vessel may be a culture bag having flexibility.

Furthermore, although the culture device 10 is configured to additionally supply the culture solution CS to the culture vessel 12 as the culture proceeds, that is, perform cell expansion in the case of the above-described embodiment, the embodiment of the present invention is not limited to this. The culture device may be configured to culture cells using a certain amount of culture solution.

That is, in a broad sense, the culture device according to the embodiment of the present invention includes a culture vessel that contains a culture solution for culturing cells, a gas supply device that supplies a gas to the culture vessel, and a humidification device that humidifies the gas flowing from the gas supply device to the culture vessel, and the humidification device includes a hollow fiber membrane filter that includes a hollow fiber membrane through which the gas from the gas supply device passes, and a casing that accommodates the hollow fiber membrane, a water supply device that fills the casing of the hollow fiber membrane filter with water, and a first heater that heats the hollow fiber membrane filter.

INDUSTRIAL APPLICABILITY

The present invention is applicable to a device which cultures cells using a culture solution in a culture vessel.

The invention claimed is:

1. A culture device, comprising:

a culture vessel that contains a culture solution for culturing cells;

a gas supply device configured to supply a gas to the culture vessel;

a humidification device configured to humidify the gas flowing from the gas supply device to the culture vessel, the humidification device comprising a hollow fiber membrane filter that includes a hollow fiber membrane configured to pass gas from the gas supply device, and a casing that accommodates the hollow fiber membrane, the casing of the hollow fiber membrane filter having a first port and a second port;

a water supply device comprising a plurality of water supply containers, the plurality of water supply containers being located above the casing; and a first heater configured to heat the hollow fiber membrane filter, wherein the water supply device is configured to supply water from a first water supply container of the plurality of water supply containers into the casing through the first port, and the water supply device is configured to move air in the casing to a second water supply container of the plurality of water supply containers through the second port.

2. The culture device according to claim 1, wherein the plurality of water supply containers are configured to have variable inner volumes.

3. The culture device according to claim 1, wherein the plurality of water supply containers are configured to store water such that all water levels in the plurality of water supply containers are at a same level.

4. The culture device according to claim 1, further comprising a second heater that is disposed below the culture vessel and is configured to heat the culture solution in the culture vessel.

5. The culture device according to claim 4, further comprising a third heater configured to heat a first membrane filter that is provided in a gas supply channel between the humidification device and the culture vessel, wherein a heating temperature of the third heater is higher than a heating temperature of the second heater.

6. The culture device according to claim 5, further comprising a fourth heater configured to heat a second membrane filter that is provided in a gas discharge channel that connects an interior of the culture vessel and outside air, wherein a heating temperature of the fourth heater is higher than a heating temperature of the second heater.

7. The culture device according to claim 6, the culture vessel having a columnar shape including a bottom plate part, a top plate part, and a sidewall part, and comprising a fifth heater configured to heat the top plate part and a sixth heater configured to heat the sidewall part, wherein heating temperatures of the fifth and sixth heaters are higher than the heating temperature of the second heater.

8. The culture device according to claim 1, further comprising a first membrane filter that is provided in a gas supply channel between the humidification device and the culture vessel, and which is disposed in a state such that a normal line of a filter surface is tilted with respect to a vertical direction.

9. The culture device according to claim 8, wherein a portion of the gas supply channel between the first membrane filter and the culture vessel extends in a horizontal direction.

10. The culture device according to claim 8, wherein the first membrane filter is located at a lower position than a connection part of the culture vessel between the gas supply channel and the culture vessel.

11. The culture device according to claim 8, further comprising a second membrane filter that is provided in a gas discharge channel that connects an interior of the culture vessel and outside air, and which is disposed in a state such that a normal line of a filter surface is tilted with respect to a vertical direction.

12. The culture device according to claim 11, wherein a portion of the gas discharge channel between the second membrane filter and the culture vessel extends in a horizontal direction.

13. The culture device according to claim 11, wherein the second membrane filter is located at a lower position than a connection part of the culture vessel between the gas supply channel and the culture vessel.

14. The culture device according claim 1, further comprising:

a culture solution supply unit configured to supply the culture solution to the culture vessel; and a control unit configured to control the gas supply device and the culture solution supply unit, wherein as an amount of the culture solution in the culture vessel supplied by the culture solution supply unit increases, the control unit is configured to change a gas supply amount per unit time of the gas supply device.

15. The culture device according to claim 14, wherein the control unit is configured to change the gas supply amount of the gas supply device such that an evaporation percentage at the culture solution amount in the culture vessel and an osmotic pressure of the culture solution calculated from the evaporation percentage take predetermined values.

16. The culture device according to claim 15, wherein the predetermined value of the osmotic pressure of the culture solution is 260 to 315 mOsm/kg.

17. The culture device according to claim 14, wherein the control unit is configured to control the heating temperature of the first heater and to change the heating temperature of the first heater as the amount of the culture solution in the culture vessel supplied by the culture solution supply unit increases.

18. The culture device according to claim 14, wherein gas supplied from the gas supply device and humidified by the humidification device is configured to be supplied to the culture vessel before the culture solution supply unit supplies the culture solution to the culture vessel.

19. The culture device according to claim 1, further comprising a culture vessel rocking unit configured to rock the culture vessel such that a portion of a surface of the culture vessel brought into contact with the culture solution moved by stirring decreases when the amount of culture solution in the culture vessel decreases.

* * * * *